(12) United States Patent
Jorgensen et al.

(10) Patent No.: US 6,569,849 B1
(45) Date of Patent: *May 27, 2003

(54) N-SUBSTITUTED AZAHETEROCYCLIC COMPOUNDS

(75) Inventors: Tine Krogh Jorgensen, Herlev (DK); Rolf Hohlweg, Kvistgaard (DE); Peter Madsen, Bagsvared (DK); Knud Erik Andersen, Smorum (DK); Svend Treppendahl, Virum (DK); Uffe Bang Olsen, Vallensbaek (DK); Zdenek Polivka, Prague (CZ); Alexandra Silhankova, Prague (CZ); Karel Sindelar, Prague (CZ); Vladimir Valenta, Prague (CZ); Tomas Kalisz, Prague (CZ)

(73) Assignee: Novo Nordisk A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/943,856

(22) Filed: Oct. 3, 1997

(30) Foreign Application Priority Data

Oct. 4, 1996 (DK) ............................................... 1089/96

(51) Int. Cl.⁷ ........................ A61K 31/55; C07D 401/06
(52) U.S. Cl. ........................ 514/217; 514/325; 540/591; 540/592; 546/203; 546/204
(58) Field of Search ..................... 540/592; 514/217

(56) References Cited

U.S. PATENT DOCUMENTS

| | | | |
|---|---|---|---|
| 3,058,979 A | 10/1962 | Ullyot et al. ................... 544/45 |
| 3,123,610 A * | 3/1964 | Cusic ......................... 540/592 |
| 3,780,035 A * | 12/1973 | Nakanishi et al. ........... 540/592 |
| 3,965,181 A | 6/1976 | Marx ......................... 564/345 |
| 5,595,989 A * | 1/1997 | Andersen et al. ............ 514/217 |
| 5,716,949 A * | 2/1998 | Andersen et al. ............ 514/211 |
| 5,916,889 A * | 6/1999 | Hohlweg et al. ............ 514/253 |
| 6,040,302 A * | 3/2000 | Hohlweg et al. ............ 514/217 |
| 6,066,632 A * | 5/2000 | Andersen et al. ............ 514/217 |

FOREIGN PATENT DOCUMENTS

| | | |
|---|---|---|
| CZ | 374682 | 3/1964 |
| DE | 1 117 584 | 11/1961 |
| DE | 1 920 170 | 1/1970 |
| DE | 2 014 911 | 10/1970 |
| DE | 2 326 401 | 12/1973 |
| DE | 2 456 098 | 6/1975 |
| DE | 3 444 837 | 6/1986 |
| FR | 1.578.748 | 7/1969 |
| FR | 2.005.201 | 12/1969 |
| FR | 2186249 * | 1/1974 |
| GB | 861420 | 2/1961 |
| WO | WO 95/18793 | 7/1995 |

OTHER PUBLICATIONS

Anderson, et al., Chemical Abstract No. 13973, vol. 38 (1962).

H.G. Morren, Chemical Abstract No. 24759' vol. 54 (1960).

McKay, et al., Journal of Pharmacological Methods, vol. 12, pp. 203–211 (Jun. 1984).

J.C.L. Fouche, Industrie Chimique belge, vol. 32, pp. 226–233 (1967).

Nakanishi et al., Journal of Medicinal Chemistry, vol. 13, No. 4, pp. 644–648 (1970).

Julou et al., Societe De Biologie, vol. 160, No. 10, pp. 1852–1858 (1966).

* cited by examiner

*Primary Examiner*—Emily Bernhardt
(74) *Attorney, Agent, or Firm*—Cheryl H. Agris; Reza Green

(57) ABSTRACT

The present invention relates to novel N-substituted azaheterocyclic compounds of the general formula

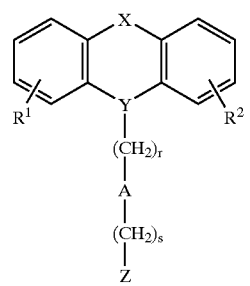

wherein X, Y, Z, A, $R^1$, $R^2$, r and s are as defined in the detailed part of the present description or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation as well as their use for treatment of indications caused by or related to secretion and circulation of insulin antagonising peptides.

8 Claims, No Drawings

N-SUBSTITUTED AZAHETEROCYCLIC COMPOUNDS

CROSS-REFERENCE TO RELATED APPLICATIONS

This application claims priority of Danish application serial no. 1089/96 filed Oct. 4, 1996, the contents of which are fully incorporated herein by reference.

FIELD OF INVENTION

The present invention relates to novel N-substituted azaheterocyclic compounds in which a substituted alkyl chain forms part of the N-substituent or salts thereof, to methods for their preparation, to compositions containing them, to the use of the compounds for preparing compositions for the clinical treatment of painful, hyperalgesic and/or inflammatory conditions in which C-fibres play a pathophysiological role by eliciting neurogenic pain or inflammation, and to methods of treating said painful, hyperalgesic and/or inflammatory conditions. The invention also relates to the use of the present compounds for reducing blood glucose and/or inhibit the secretion, circulation or effect of insulin antagonising peptides like CGRP or amylin, the present compounds being known to interfere with neuropeptide containing C-fibres. Hence the present compounds can be used in the treatment of insulin resistance in non-insulin-dependent diabetes mellitus (NIDDM) in order to improve the glucose tolerance as well as ageing-associated obesity.

BACKGROUND OF INVENTION

The nervous system exerts a profound effect on the inflammatory response. Antidromic stimulation of sensory nerves results in localised vasodilation and increased vascular permeability (Janecso et al. Br. J. Pharmacol. 1967, 31, 138–151) and a similar response is observed following injection of peptides known to be present in sensory nerves. From this and other data it is postulated that peptides released from sensory nerve endings mediate many inflammatory responses in tissues like skin, joint, urinary tract, eye, meninges, gastrointestinal and respiratory tracts. Hence inhibition of sensory nerve peptide release and/or activity, may be useful in treatment of, for example arthritis, dermatitis, rhinitis, asthma, cystitis, gingivitis, thrombophlelitis, glaucoma, gastrointestinal diseases or migraine.

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficking in physiological conditions, such as exercise, and may also contribute to the decreased insulin action and skeletal muscle glycogen synthase in pathophysiological conditions like NIDDM or ageing-associated obesity (Melnyk et al. Obesity Res. 3, 337–344, 1995) where circulating plasma levels of CGRP are markedly increased. Hence inhibition of release and/or activity of the neuropeptide CGRP may be useful in the treatment of insulin resistance related to type 2 diabetes or ageing.

In U.S. Pat. No. 4,383,999 and U.S. Pat. No. 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake.

WO 9518793 discloses N-substituted azaheterocyclic compounds in which an unsubstituted alkyl chain containing from 2 to 4 carbon atoms forms part of the N-substituent.

SUMMARY OF THE INVENTION

The present invention relates to compounds of the general formula I, wherein X, Y, Z, $M_1$, $M_2$, $R^1$ through $R^{20}$, r, s, n, m and p are as defined in the detailed part of the present description.

The present compounds are useful for the treatment, prevention, elimination, alleviation or amelioration of an indication related to all painful, hyperalgesic and/or inflammatory conditions in which C-fibres play a pathophysiological role, e.g. neurogenic pain, inflammation, migraine, neuropathy, itching and rheumatoid arthritis, as well as indications caused by or related to the secretion and circulation of insulin antagonising peptides, e.g. non-insulin-dependent diabetes mellitus (NIDDM) and ageing-associated obesity.

In another aspect, the present invention includes within its scope pharmaceutical compositions comprising, as an active ingredient, at least one of the compounds of the general formula I or a pharmaceutically acceptable salt thereof together with a pharmaceutically acceptable carrier or diluent.

In another aspect of the present invention there is provided a method of treating painful, hyperalgesic and/or inflammatory conditions in which C-fibres play a pathophysiological role, e.g. neurogenic pain, inflammation, migraine, neuropathy, itching and rheumatoid arthritis, as well as a method of treating indications caused by or related to the secretion and circulation of insulin antagonising peptides like CGRP or amylin, e.g. non-insulin-dependent diabetes mellitus (NIDDM) and ageing-associated obesity. The method of treating may be described as the treatment of one of the above indications in a subject in need thereof, which comprises the step of administering to the said subject a neurologically effective amount of a compound of the invention, or a pharmaceutically acceptable salt thereof.

A further aspect of the invention relates to the use of a compound of the present invention for the preparation of a pharmaceutical composition for the treatment of all painful, hyperalgesic and/or inflammatory conditions in which C-fibres play a pathophysiological role, e.g. neurogenic pain, inflammation, migraine, neuropathy, itching and rheumatoid arthritis, as well as for the treatment of indications caused by or related to the secretion and circulation of insulin antagonising peptides, e.g. non-insulin-dependent diabetes mellitus (NIDDM) and ageing-associated obesity.

Further objects will become apparent from the following description.

DETAILED DESCRIPTION OF THE INVENTION

Accordingly, the present invention relates to novel N-substituted azaheterocyclic compounds of formula I

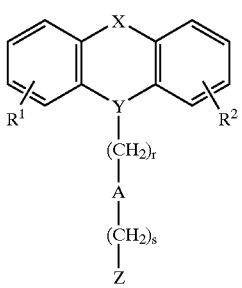

(I)

wherein R¹ and R² independently are hydrogen, halogen, trifluoromethyl, hydroxy, $C_{1-6}$-alkyl or $C_{1-6}$-alkoxy; and X is ortho-phenylene, —O—, —S—, —C(R³R⁴)—, —CH₂CH₂—, —CH═CH—CH₂—, —CH₂—CH═CH—, —CH₂—(C═O)—, —(C═O)—CH₂—, —CH₂CH₂CH₂—, —CH═CH—, —N(R⁵)—(C═O)—, —(C═O)—N(R⁵)—, —O—CH₂—, —CH₂—O—, —O—CH₂—O—, —CH₂—O—CH₂—, —S—CH₂—, —CH₂—S—, —(CH₂)N(R⁵)—, —N(R⁵)(CH₂)—, —N(CH₃)SO₂—, —SO₂N(CH₃)—, —CH(R⁶)CH₂—, —CH₂CH(R⁶)—, —(C═O)—, —(R⁷)— or —(S═O)— wherein R³, R⁴, R⁵ and R⁷ independently are hydrogen or $C_{1-6}$-alkyl; and wherein R⁶ is $C_{1-6}$-alkyl or phenyl; and Y is >N—, >CH—, >N—(C═O)— or >C═C(R⁸)—, wherein only the underscored atom participates in the ring system and wherein R⁸ is hydrogen or $C_{1-6}$-alkyl; and A is —CH═CR⁹—, —CR⁹═CH—, —C≡C—, —(C═O)—, —(C═CH₂)—, —(CR⁹R¹⁰)—, —CH(OR¹¹)—, —CH(NHR¹¹)—, phenylene, $C_{3-7}$-cycloalkylene or the completion of a bond wherein R⁹ and R¹⁰ independently are hydrogen, $C_{1-6}$-unbranched alkyl, $C_{3-6}$-branched alkyl or $C_{3-7}$-cycloalkyl and wherein R¹¹ is hydrogen or $C_{1-6}$ alkyl; and r and s independently are 0, 1, 2, 3 or 4; and Z is selected from

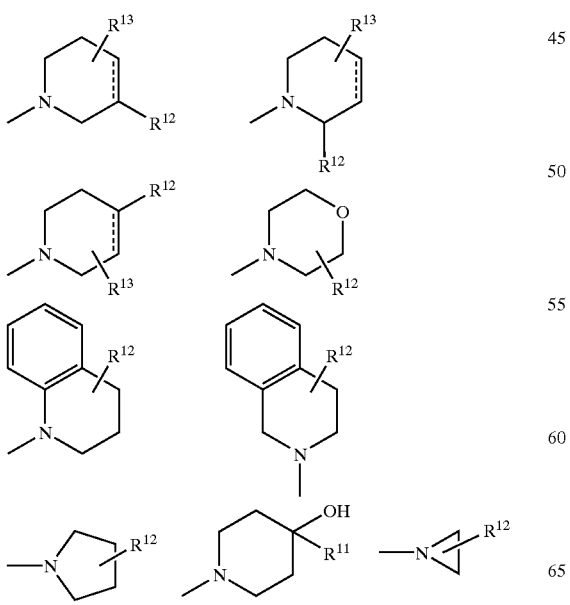

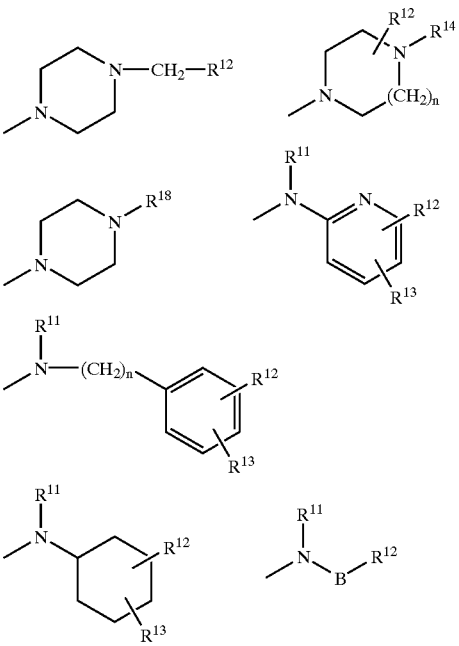

wherein n is 0, 1 or 2; and

R¹¹ is hydrogen, $C_{1-6}$-alkyl, $C_{1-6}$-alkoxy or phenyl optionally substituted with halogen, triflouromethyl, hydroxy, $C_{1-6}$-alkyl or $C_{1-6}$-alkoxy; and R¹² is —(CH₂)$_m$OH or —(CH₂)$_p$COR¹⁷ wherein m is 0, 1, 2, 3, 4, 5 or 6 and p is 0 or 1; and wherein R¹⁷ is —OH, —NHR²⁰ or $C_{1-6}$-alkoxy, wherein R²⁰ is hydrogen or $C_{1-6}$-alkyl; and R¹³ is hydrogen, halogen, trifluoromethyl, hydroxy, $C_{1-6}$-alkyl or $C_{1-6}$-alkoxy; and R¹⁴ is hydrogen or $C_{1-6}$-alkyl; and B is $C_{1-6}$-alkylene, $C_{2-6}$-alkenylene or $C_{2-6}$-alkynylene; and ..... is optionally a single bond or a double bond; and R¹⁸ is selected from

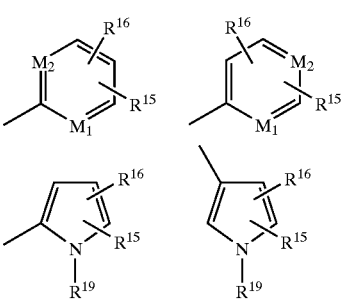

wherein M₁ and M₂ independently are C or N; and

R¹⁹ is hydrogen, $C_{1-6}$-alkyl, phenyl or benzyl; and

R¹⁵ is hydrogen, halogen, trifluoromethyl, nitro or cyano; and

R¹⁶ is hydrogen, halogen, trifluoromethyl, nitro, cyano, —(CH₂)$_m$COR¹⁷, —(CH₂)$_m$OH or —(CH₂)$_m$SO₂R¹⁷, wherein m is 0, 1 or 2; or $R^{16}$ is selected from

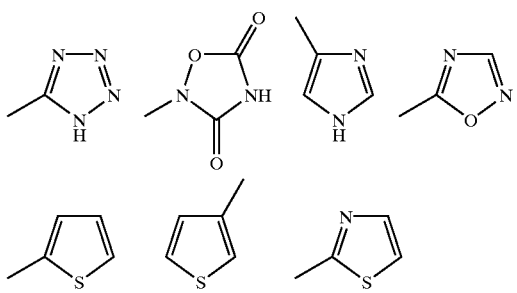

or a pharmaceutically acceptable salt thereof.

Compounds of formula I wherein Y is >$\underline{C}$=CH—, A is —CH$_2$— and r+s≦2, or Y is >$\underline{C}$=CH—, A is the completion of a bond and r+s≦3, or Y is >$\underline{N}$— or >$\underline{C}$H—, A is —CH$_2$— and r+s≦3, or Y is >$\underline{N}$— or >$\underline{C}$H—, A is the completion of a bond and r+s≦4, and Z is selected from

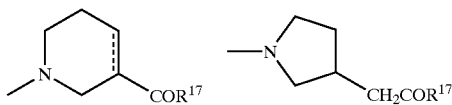

wherein $R^{17}$ is —OH or $C_{1-6}$-alkoxy, are known from WO 9518793.

The compounds of formula I may exist as geometric and optical isomers and all isomers, as separated, pure or partially purified stereoisomers or racemic mixtures thereof are included in the scope of the invention. Isomers may be separated by means of standard methods such as chromatographic techniques or fractional crystallisation of suitable salts.

Preferably, the compounds of formula I exist as the individual geometric or optical isomers.

The compounds according to the invention may optionally exist as pharmaceutically acceptable acid addition salts or—when the carboxylic acid group is not esterified—as pharmaceutically acceptable metal salts or—optionally alkylated—ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts, and include the pharmaceutically acceptable salts listed in Journal of Pharmaceutical Science, 66, 2 (1977) which are known to the skilled artisan.

Also included are the hydrates of the above mentioned acid addition salts which the present compounds are able to form.

The acid addition salts may be obtained as the direct products of compound synthesis. In the alternative, the free base may be dissolved in a suitable solvent containing the appropriate acid, and the salt isolated by evaporating the solvent or by precipitation or crystallisation.

The compounds of formula I may be administered in a pharmaceutically acceptable acid addition salt form or where possible as a metal or a lower alkylammonium salt. Such salt forms exhibit approximately the same order of activity as the free base forms.

In the above structural formula and throughout the present specification, the following terms have the indicated meaning:

The term "$C_{1-6}$-alkyl" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-hexyl, 1,2-dimethylpropyl, 2,2-dimethylpropyl and 1,2,2-trimethylpropyl.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "halogen" means fluorine, chlorine, bromine or iodine.

In a preferred embodiment of the invention $R^1$ and $R^2$ are selected from hydrogen halogen, trifluoromethyl or $C_{1-6}$-alkyl. Preferably $R^1$ and $R^2$ are hydrogen, chloro or methyl.

In a another preferred embodiment of the invention X is selected from —O—, —S—, —CH$_2$CH$_2$—, —CH=CH—, —O—CH$_2$—, —CH$_2$—O—, —OCH$_2$O—, —S—CH$_2$— or —CH$_2$—S—. Preferably X is —CH$_2$CH$_2$—, —O—CH$_2$— or —CH$_2$—O—.

In another preferred embodiment of the invention Y is selected from >$\underline{N}$—, >$\underline{C}$H—, >$\underline{N}$— (C=O)— or >$\underline{C}$=C($R^8$)—, wherein only the underscored atom participates in the ring system and wherein $R^8$ is hydrogen or methyl.

In another preferred embodiment of the invention A is selected from —CH=CR$^9$—, —CR$^9$=CH—, —C≡C—, —(C=O)—, —(CR$^9$R$^{10}$)—, —CH(OR$^{11}$)—, phenylene or the completion of a bond, wherein $R^9$ and $R^{10}$ independently are hydrogen, $C_{1-6}$-unbranched alkyl, and wherein $R^{11}$ is hydrogen or $C_{1-6}$ alkyl.

In another preferred embodiment of the invention r is 0, 1 or 2.

In another preferred embodiment of the invention s is 0, 1 or 2.

In another preferred embodiment of the invention Z is selected from

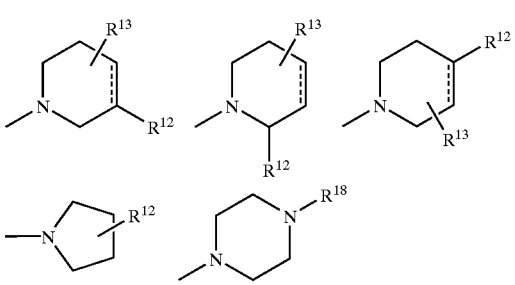

wherein $R^{12}$, $R^{13}$ and $R^{18}$ are as defined above.

In another preferred embodiment of the invention $R^{12}$ is —(CH$_2$)$_p$COR$^{17}$ wherein p is 0 or 1 and $R^{17}$ is —OH.

In another preferred embodiment of the invention $R^{18}$ is

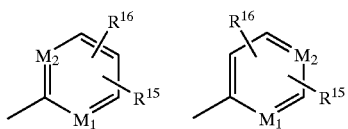

wherein $M_1$ and $M_2$, $R^{15}$ and $R^{16}$ are as defined above.

In yet another preferred embodiment of the invention $R^{16}$ is $(CH_2)_m COR^{17}$ wherein m is 0 or 1 and $R^{17}$ is —OH.

Preferred compounds of the present invention include:
1-(3-(10,11-Dihydro-5H-dibenzo[b,f]azepin-5-yl)-(2R)-methyl-1-propyl)-(3R)-piperidinecarboxylic acid;
1-(3-(10,11-Dihydro-5H-dibenzo[b,d]azepin-5-yl)-(2R)-methyl-1-propyl)-4-piperidinecarboxylic acid;
1-(3-(10,11-Dihydro-5H-dibenzo[b,f]azepin-5-yl)-(2R)-methyl-1-propyl)-(2R)-piperidinecarboxylic acid;
1-(4-(10,11-Dihydro-5H-dibenzo[b,f]azepin-5-yl)-(2Z)-butenyl)-(3R)-piperidinecarboxylic acid;
1-(3-(10,11-Dihydro-5H-dibenzo[a,d]cyclohepten-5-ylidene)-1-propionyl)-(3R)-piperidinecarboxylic acid;
1-(2-(10,11-Dihydro-5H-dibenzo[a,d]cyclohepten-5-yl)-1-ethyl)-(3R)-piperidinecarboxylic acid;
1-(4-(10,11-Dihydro-5H-dibenzo[b,f]azepin-5-yl)-(2E)-butenyl)-(3R)-piperidinecarboxylic acid;
1-(2-(10,11-Dihydro-5H-dibenzo[b,f]azepin-5-yl)-1-methyl-1-ethyl)-(3R)-piperidinecarboxylic acid;
1-(3-(10,11-Dihydro-5H-dibenzo[b,f]azepin-5-yl)-2-methyl-3-oxopropyl)-(3R)-piperidinecarboxylic acid;
1-(4-(10,11-Dihydro-5H-dibenzo[b,f]azepin-5-yl)-2-butynyl)-(3R)-piperidinecarboxylic acid;
1-(3-(10,11-Dihydro-5H-dibenzo[b,f]azepin-5-yl)-1-methyl-1-propyl)-(3R)-piperidinecarboxylic acid;
1-(3-(10,11-Dihydro-5H-dibenzo[b,f]azepin-5-yl)-2-hydroxy-1-propyl)-(3R)-piperidinecarboxylic acid;
1-(2-(10,11-Dihydro-dibenzo[b,f]azepin-5-ylmethyl)-1-pentyl)-(3R)-piperidinecarboxylic acid;
1-(3-(3-Chloro-10,11-dihydro-5H-dibenzo[b,d]azepin-5-yl)-(2R)-methyl-1-propyl)-(3-piperidinecarboxylic acid;
1-(3-(3-Trifluoromethyl-10,11-dihydro-5H-dibenzo[b,f]azepin-5-yl)-(2R)-methyl-1-propyl)-(3R)-piperidinecarboxylic acid;
1-(3-(3-Methyl-10,11-dihydro-5H-dibenzo[b,f]azepin-5-yl)-(2R)-methyl-1-propyl)-(3R)-piperidinecarboxylic acid;
1-(3-(3-Methoxy-10,11-dihydro-5H-dibenzo[b,f]azepin-5-yl)-(2R)-methyl-1-propyl)-(3R)-piperidinecarboxylic acid;
1-(3-(2-Chloro-10,11-dihydro-5H-dibenzo[b,d]azepin-5-yl)-(2R)-methyl-1-propyl)-(3R)-piperidinecarboxylic acid;
2-(4-(3-(10,11-Dihydro-5H-dibenzo[b,f]azepin-5-yl)-(2R)-methyl-1-propyl)-1-piperazinyl)-nicotinic acid;
1-(2-(10,11-Dihydro-5H-dibenzo[a,d]cyclohepten-5-ylidene)-1-propyl)-(3R)-piperidinecarboxylic acid;
1-(2-(10,11-Dihydro-5H-dibenzo[b,f]azepin-5-yl)-cyclopropylmethyl)-(3R)-piperidinecarboxylic acid;
1-(2-(10,11-Dihydro-5H-dibenzo[b,f]azepin-5-yl)-cyclopentylmethyl)-(3R)-piperidinecarboxylic acid;
1-(2-(10,11-Dihydro-5H-dibenzo[a,d]cyclohepten-5-yl)-1-ethyl)-(3R)-piperidinecarboxylic acid;
(R)-1-(3-(10,11-Dihydro-5H-dibenzo[b,f]azepin-5-yl)-3-oxopropyl)-3-piperidinecarboxylic acid;
(R)-1-(4-(10,11-Dihydro-5H-dibenzo[a,d]cyclohepten-5-yl)-benzyl)-3-piperidinecarboxylic acid;
(R)-1-(4-(10,11-Dihydro-5H-dibenzo[b,f]azepin-5-yl)-2-butyn-1-yl)-3-piperidinecarboxylic acid;
(R)-1-((2R)-Methyl-3-(3-methyl-10,11-dihydro-5H-dibenzo[b,f]azepin-5-yl)-1-propyl)-4-piperidinecarboxylic acid;
(R)-1-(3-(10,11-Dihydro-5H-dibenzo[b,f]azepin-5-yl)1-methylpropyl)-3-piperidinecarboxylic acid;
(R)-1-(2-(10,11-dihydro-5H-dibenzo[b,f]azepin-5-yl)-1-methyl-ethyl)-3-piperidinecarboxylic acid;
(R)-1-(2-(10,11-Dihydro-5H-dibenzo[a,d]cyclohepten-5-ylidene)-1-propyl)-3-piperidinecarboxylic acid;
(R)-1-(10,11-Dihydro-5H-dibenzo[a,d]cyclohepten-5-yl) methyl)-3-piperidinecarboxylic acid;
1-(3-(10,11-Dihydro-5H-dibenzo[b,f]azepin-5-yl)-(2R)-methyl-1-propyl)-3-pyrrolidinylacetic acid:
2-(1-(3-(10,11-Dihydrodibenzo[b,f]azepin-5-yl)-(2R)-methylpropyl)-4-piperazinyl)-nicotinic acid;
(R)-1-(2-(10,11-Dihydro-5H-dibenzo[b,f]azepin-5-ylmethyl)-1-pentyl)-3-piperidinecarboxylic acid;
2-(4-(3-(10,11-Dihydro-5H-dibenzo[b,f]azepin-5-yl)-2-hydroxypropyl)piperazin-1-yl)nicotinic acid;
1-(3-(10,11-Dihydro-5H-dibenzo[b,f]azepin-5-yl)-2-methyl-3-oxo-propyl)-3-piperidinearboxylic acid;
(R)-1-(3-(10,11-Dihydro-5H-dibenzo[b,f]azepin-5-yl)-1-propionyl)-3-piperidinecarboxylic acid;
1-(3-(10,11-Dihydro-5H-dibenzo[b,f]azepin-5-yl)-1-propionyl)-4-piperidinecarboxylic acid;
(R)-1-(2-(10,11-Dihydro-5H-dibenzo[b,f]azepin-5-ylcarbonyl)-1-benzyl)-3-piperidinecarboxylic acid;
(R)-1-(2-(10,11-Dihydro-5H-dibenzo[b,f]azepin-5-ylmethyl)-benzyl)-3-piperidinecarboxylic acid;
(R)-1-(3-(10,11-Dihydro-5H-dibenzo[a,d]cyclohepten-5-yl)-3-oxo-1-propyl)-3-piperidinecarboxylic acid;
1-(3-(3-Chloro-10,11-dihydro-5H-dibenzo[b,f]azepin-5-yl)-(2R)-methylpropyl)-4-piperidine carboxylic acid;
(3-(10,11-Dihydro-5H-dibenzo[b,f]azepin-5-yl)-2-hydroxypropyl)-4-piperidinecarboxylic acid;
(R)-1-(3-(10,11-Dihydro-5H-dibenzo[b,f]azepin-5-yl)-2-hydroxypropyl)-3-piperidinecarboxylic acid;
1-(3-(10,11-Dihydro-5H-dibenzo[b,f]azepin-5-yl)-2-propoxypropyl)-4-piperidinecarboxylic acid;
(R)-1-(2-(N-(10,11-dihydro-5H-dibenzo[a,d]cyclohepten-5-yl)-N-methylamino)ethyl)-3-piperidinecarboxylic acid;
or a pharmaceutically acceptable salt thereof.

It has been demonstrated that the novel compounds of formula I inhibit neurogenic inflammation which involves the release of neuropeptides from peripheral and central endings of sensory C-fibres. Experimentally this can be demonstrated in animal models of histamine induced paw oedema (Amann et al, Europ. J. Pharmacol. 279, 227–231, 1995) in which the novel compounds of formula I exhibit a potent inhibitory effect. Compounds of formula I may be used to treat all painful, hyperalgesic and/or inflammatory conditions in which C-fibres play a pathophysiological role by eliciting neurogenic pain or inflammation, i.e.:

Acutely painful conditions exemplified by migraine, post-operative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, itching, chronic pancreatitis, inflammatory skin disease including psoriasis and autoimmune dermatoses, osteoporotic pain.

Further, it has been demonstrated that the compounds of general formula I improve the glucose tolerance in diabetic ob/ob mice and that this may result from the reduced release of CGRP from peripheral nervous endings. Hence the compounds of general formula I may be used in the treatment of NIDDM as well as ageing-associated obesity. Experimentally this has been demonstrated by the subcutaneous administration of glucose into ob/ob mice with or without previous oral treatment with a compound of general formula I.

The compounds of formula I may be prepared by the following method:

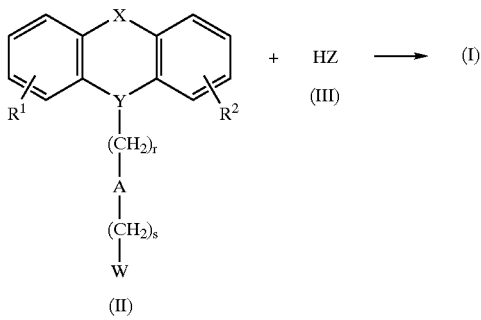

A compound of formula II wherein $R^1$, $R^2$, X, Y, A, r and s are as defined above and W is a suitable leaving group such as halogen, p-toluene sulphonate or mesylate may be reacted with an aza compound of formula III wherein Z is as defined above. This alkylation reaction may be carried out in a solvent such as acetone, dibutylether, 2-butanone, methyl ethyl ketone, ethyl acetate, tetrahydrofuran (THF) or toluene in the presence of a base e.g. sodium hydride or potassium carbonate and a catalyst, e.g. an alkali metal iodide at a temperature up to reflux temperature for the solvent used for e.g. 1 to 120 h. If esters have been prepared in which $R^{17}$ is alkoxy, compounds of formula I wherein $R^{17}$ is OH may be prepared by hydrolysis of the ester group, preferably at room temperature in a mixture of an aqueous alkali metal hydroxide solution and an alcohol such as methanol or ethanol, for example, for about 0.5 to 6 h.

Compounds of formula II and III may readily be prepared by methods familiar to those skilled in the art.

Under certain circumstances it may be necessary to protect the intermediates used in the above methods e.g. a compound of formula III with suitable protecting groups. The carboxylic acid group can, for example, be esterified. Introduction and removal of such groups is described in "Protective Groups in Organic Chemistry" J. F. W. McOrnie ed. (New York, 1973).

PHARMACOLOGICAL METHODS

I. Histamine Induced Paw Oedema

The rat histamine paw oedema test was performed essentially as described by Amann et al. (Europ. J. Pharmacol. 279, 227–231, 1995). In brief 250–300 g male Sprague-Dawley rats were anaesthetized with pentobarbital sodium, and placed on a 32 degree (Celsius) heated table. Ten minutes later histamine (50 micoliter, 3 mg/ml) was injected in the right hind paw and 20 minutes hereafter the paw swelling was determined by water plethysmography (Ugo Basile). Test compounds were administered intraperitoneally at 15 minutes before the anaesthetics.

II. Reduced Release of CGRP ob/ob female mice, 16 weeks of age, where injected glucose (2 g/kg) subcutaneously. At times hereafter blood glucose was determined in tail venous blood by the glucose oxidase method. At the end of the study the animals were decapitated and trunk blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

Values for inhibition of histamine induced oedema response for some representative compounds are recorded in table 1.

TABLE 1

Inhibition of histamin induced pain response at 1.0 mg/kg

| Example no. | % Oedema inhibition |
|---|---|
| 3 | 47 |
| 4 | 26 |

PHARMACEUTICAL COMPOSITIONS

The present invention also relates to pharmaceutical compositions comprising a compound of formula I or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatine, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

The route of administration may be any route which effectively transports the active compound to the appropriate or desired site of action, such as oral, nasal, pulmonary or parenteral e.g. rectal, depot, transdermal, subcutaneous, intranasal, intramuscular, topical, intravenous, intraurethral, ophthalmic solution or an ointment, the oral route being preferred.

If a solid carrier for oral administration is used, the preparation can be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilising agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques contains

| Core: | |
|---|---|
| Active compound (as free compound or salt thereof) | 100 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC approx. | 9 mg |
| *Mywacett ® 9-40 T approx. | 0.9 mg |

*Acylated monoglyceride used as plasticizer for film coating.

The compounds of the invention may be administered to a mammal, especially a human, in need of such treatment, prevention, elimination, alleviation, or amelioration of an indication related to all painful, hyperalgesic and/or inflammatory conditions in which C-fibres play a pathophysiological role such as e.g. neurogenic pain, inflammation, migraine, neuropathy, itching and rheumatoid arthritis, as well as indications caused by or related to the secretion and circulation of insulin antagonising peptides, such as non-insulin-dependent diabetes mellitus (NIDDM) or ageing-associated obesity. Such mammals include also animals, both domestic animals, e.g. household pets, and non-domestic animals such as wildlife.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

Suitable dosage ranges varies as indicated above depending as usual upon the exact mode of administration, form in which administered, the indication towards which the administration is directed, the subject involved and the body weight of the subject involved, and the preference and experience of the physician or veterinarian in charge.

Generally, the compounds of this invention are dispensed in unit dosage form comprising 50–200 mg of active ingredient in or together with a pharmaceutically acceptable carrier per unit dosage.

Usually, dosage forms suitable for oral, nasal, pulmonal or transdermal administration comprise from about 0.5 mg to about 1000 mg, preferably from about 1 mg to about 500 mg of the compounds of formula I admixed with a pharmaceutically acceptable carrier or diluent.

Any novel feature or combination of features described herein is considered essential to this invention.

EXAMPLES

The process for preparing compounds of formula I and preparations containing them is further illustrated in the following examples, which, however, are not to be construed as limiting.

Hereinafter, TLC is thin layer chromatography, CDCl$_3$ is deutero chloroform and DMSO-d$_6$ is hexadeutero dimethylsulfoxide. The structures of the compounds are confirmed by either elemental analysis or NMR, where peaks assigned to characteristic protons in the title compounds are presented where appropriate. $^1$H NMR shifts ($\delta_H$) are given in parts per million (ppm). M.p. is melting point and is given in ° C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

Example 1

1-(3-(10,11-Dihydro-5H-dibenzo[b,f]azepin-5-yl)-(2R)-methyl-1-propyl)-(3R)-piperidinecarboxylic Acid Hydrochloride

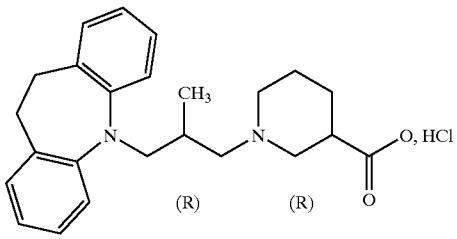

To a solution of iminodibenzyl (32.9 g, 0.170 mol) in dry N,N-dimethylformamide (500 ml) kept under an atmosphere of nitrogen, sodium hydride (8.77 g, 0.220 mol, 60% dispersion in oil) was added in portions. The reaction mixture was stirred for 2.5 h at room temperature. 2-(3-Bromo-(2R)-methylpropoxy)tetrahydropyran (46.0 g, 0.194 mol) was dissolved in N,N-dimethylformamide (100 ml) and added, and the reaction mixture was stirred for 36 h at 50° C. After cooling, dichloromethane (500 ml) was added followed by water (500 ml), and the phases were separated. The aqueous phase was extracted with dichloromethane (500 ml), and the combined organic extracts were washed with water (500 ml), dried (MgSO$_4$) and evaporated in vacuo. The residue was purified by column chromatography on silica gel using dichloromethane as eluent. This afforded 4.4 g of 5-((2S)-methyl-3-(tetrahydropyran-2-yloxy)-1-propyl)-10,11-dihydro-5H-dibenzo[b,f]azepine.

The above tetrahydropyran (4.4 g, 12.5 mmol) was dissolved in ethanol (100 ml) and pyridinium-p-toluenesulfonate (0.47 g, 1.9 mmol) was added. The mixture was heated at 50° C. overnight. After cooling, the mixture was evaporated. The residue was dissolved in dichloromethane (120 ml), and diethyl ether (40 ml) and water (90 ml) was added. The phases were separated and the organic phase was washed with diluted (50%) brine (90 ml). The brine phase was extracted with dichloromethane (50 ml). The combined organic extracts were dried (MgSO$_4$) and evaporated to give 3.42 g (75%) of 3-(10,11-dihydro-5H-dibenzo[b,f]azepin-5-yl)-(2S)-methyl-1-propanol.

The above alcohol (3.42 g, 12.8 mmol) was dissolved in toluene (100 ml) and cooled on an icebath. Methanesulfonyl chloride (2.0 ml, 25 mmol) was added followed by triethyl amine (4.5 ml, 32 mmol). The icebath was removed, and the mixture was diluted with toluene (100 ml). The reaction mixture was stirred for 1 h at room temperature. The mixture was transferred to a separation funnel, diluted with toluene (100 ml) and washed with water (150 ml). The aqueous phase was extracted with toluene (100 ml). The combined organic extracts were washed with brine (2×100 ml), dried (MgSO$_4$) and evaporated. The residue was dissolved in acetonitrile (20 ml) and added to a solution of (R)-3-piperidinecarboxylic acid ethyl ester tartrate (5.76 g, 19.2 mmol) and diisopropylethylamine (6.6 ml, 38 mmol) in acetonitrile (60 ml). The resulting mixture was heated at reflux temperature for 64 h. After cooling, the reaction mixture was transferred to a separation funnel and water (75 ml) was added, followed by brine (10 ml). The phases were separated and the aqueous phase was extracted with ethyl acetate (100 ml+50 ml). The combined organic extracts were washed with brine (75 ml), dried (MgSO$_4$) and evaporated. The residue was purified by column chromatography on silica gel using a mixture of heptane and ethyl acetate (3:1) as eluent. This afforded 1.8 g (35%) of 1-(3-(10,11-dihydro-5H-dibenzo[b,f]azepin-5-yl)-(2R)-methyl-1-propyl)-(3R)-piperidinecarboxylic acid ethyl ester as an oil.

The above ethyl ester (1.2 g, 3.0 mmol) was dissolved in ethanol (75 ml). Sodium hydroxide (0.7 g, 18 mmol) dissolved in water (8 ml) was added, and the reaction mixture was stirred for 3.5 h at room temperature. Using 1 M hydrochloric acid (22 ml), pH was adjusted to 2.5. The mixture was transferred to a separation funnel, water (100 ml) was added, and the phases were separated. The aqueous phase was extracted with dichloromethane (50 ml), and the combined organic phases were washed with brine (150 ml), dried (MgSO$_4$) and evaporated. The residue was transferred to a smaller flask using a mixture of dichloromethane and acetone, and the solvents were evaporated. The resulting solid was suspended in isopropyl acetate, left stirring for 6 h, filtered off and dried. Yield 1.03 g (84%) of the title compound as an amorphous powder.

HPLC retention time=23.25 minutes (5 μm C18 4×250 mm column, eluting with a 20–80% gradient of 0.1% trifluoroacetic acid/acetonitrile and 0.1% trifluoroacetic acid/water over 30 minutes at 35° C.). Calculated for C$_{24}$H$_{30}$N$_2$O$_2$, HCl, 0.5 H$_2$O: C, 67.98%; H, 7.61%; N, 6.60%; Found: C, 67.99%; H, 7.64%; N, 6.40%.

Example 2

1-(3-(10,11-Dihydro-5H-dibenzo[b,f]azepin-5-yl)-(2R)-methyl-1-propyl)-4-piperidinecarboxylic Acid Hydrochloride

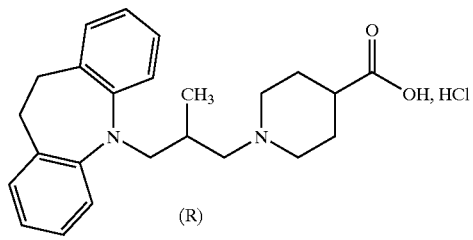

To a solution of iminodibenzyl (2.75 g, 14 mmol) in dry benzene (25 ml), sodium amide (0.55 g, 14 mmol) was added, and the mixture was heated at 80° C. for 1 h. 2-(3-Bromo-(2R)-methylpropoxy)tetrahydropyran (3.3 g, 14 mmol) was added and heating was continued for 20 h. After cooling to room temperature, water (10 ml) was added, and the phases were separated. The organic phase was evaporated until dryness. The residue was dissolved in a mixture of methanol (40 ml) and 4 N hydrochloric acid (15 ml). The mixture was heated at reflux temperature for 15 minutes, methanol was evaporated off and the residue was extracted with benzene (50 ml). The organic extract was dried (K$_2$CO$_3$), filtered and the solvent evaporated in vacuo. This afforded a residue which was purified by chromatography on silica gel using first chloroform and then ethyl acetate as eluent. This afforded 1.45 g of 3-(10,11-dihydro-5H-dibenzo[b,f]azepin-5-yl)-(2S)-methyl-1-propanol as an oil.

The above alcohol (1.45 g, 5.4 mmol) was dissolved in benzene (25 ml) and triethylamine (1.5 ml) was added. Methanesulfonyl chloride (0.75 g, 6.5 mmol) was added and the reaction mixture was stirred for 6 h. Water was added and the phases were separated. The organic phase was dried (MgSO$_4$) and the solvent was evaporated in vacuo. The residue was dissolved in methyl ethyl ketone (50 ml), and 4-piperidinecarboxylic acid ethyl ester (1.4 g, 8.9 mmol) and potassium carbonate (1.0 g, 7.25 mmol) were added, and the mixture was heated at reflux temperature for 20 h. The mixture was filtered and the solvent evaporated in vacuo to give a residue which was purified by chromatography on silica gel (30 g) using ethyl acetate as eluent. This afforded 1.25 g of 1-(3-(10,11-dihydro-5H-dibenzo[b,f]azepin-5-yl)-(2R)-methyl-1-propyl)-4-piperidinecarboxylic acid ethyl ester as an oil.

The above ester (1.25 g, 3.1 mmol) was dissolved in ethanol (20 ml) and 5 N sodium hydroxide (2 ml) was added. The mixture was stirred at room temperature for 3 days, and ethanol was evaporated in vacuo. Water (20 ml) followed by acetic acid (1.5 ml) were added, and the mixture was extracted with dichloromethane (50 ml). The organic extract was dried (MgSO$_4$), and the solvent was evaporated in vacuo. The resulting foamy residue was dissolved in a mixture of acetone and diethyl ether and treated with hydrochloric acid in diethyl ether. This afforded 0.45 g of the title compound as a crystaline solid.

M.p. 224–230° C. Calculated for C$_{24}$H$_{30}$N$_2$O$_2$, HCl, 0.25 H$_2$O: C, 68.72%; H, 7.57%; Cl, 8.45%; N, 6.68%; Found: C, 68.92%; H, 7.56%; Cl, 8.41%; N, 6.45%.

Example 3

1-(3-(10,11-Dihydro-5H-dibenzo[b,f]azepin-5-yl)-(2R)-methyl-1-propyl)-(2R)-piperidinecarboxylic Acid Hydrochloride

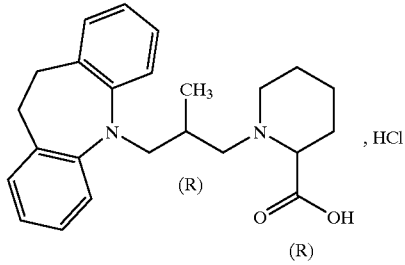

To a solution of iminodibenzyl (2.75 g, 14 mmol) in dry benzene (25 ml) sodium amide (0.55 g, 14 mmol) was added and the mixture was stirred and heated at 80° C. for 1 h. (3-Bromo-(2R)-methylpropoxy)tetrahydropyran (3.3 g, 14 mmol) was added and stirring and heating was continued for 20 h. After cooling to room temperature, water (10 ml) was added, and the phases were separated. The organic phase was evaporated until dryness. The residue was dissolved in a mixture of methanol (40 ml) and 4 N hydrochloric acid (15 ml). The mixture was then heated at reflux temperature for 15 minutes, methanol was evaporated and the residue was extracted with benzene (50 ml). The organic extract was dried ($K_2CO_3$), filtered and the solvent was evaporated in vacuo. This afforded a residue which was purified further by chromatography on silica gel (40 g) using first chloroform and then ethyl acetate as eluent to give 1.45 g of 3-(10,11-dihydro-5H-dibenzo[b,f]azepin-5-yl)-(2S)-methyl-1-propanol as an oil.

The above alcohol (1.45 g, 5.4 mmol) was dissolved in benzene (25 ml) and triethylamine (1.5 ml) was added. Methanesulfonyl chloride (0.75 g, 6.5 mmol) was added and the reaction mixture was stirred for 6 h. Water was added and the phases were separated. The organic phase was dried ($MgSO_4$) and the solvent evaporated in vacuo to give a residue which was dissolved in N,N-dimethylformamide (10 ml). (R)-2-Piperidinecarboxylic acid ethyl ester hydrochloride (1.05 g, 5.4 mmol) and potassium carbonate (1.8 g, 13 mmol) were added, and the mixture was heated at 100° C. for 10 h. After cooling, the mixture was diluted with water and extracted with benzene (50 ml). The organic phase was dried ($K_2CO_3$), filtered and the solvent evaporated in vacuo to give a residue which was purified by chromatography on silica gel (30 g) using chloroform as eluent. This afforded 0.80 g of 1-(3-(10,11-dihydro-5H-dibenzo[b,f]azepin-5-yl)-(2R)-methyl-1-propyl)-(2R)-piperidinecarboxylic acid ethyl ester as an oil.

The above ester (0.80 g, 2 mmol) was dissolved in ethanol (20 ml) and 5 N sodium hydroxide (2 ml) was added. The mixture was stirred at room temperature for 7 days, ethanol was evaporated in vacuo, water (20 ml) was added and the mixture was washed with diethyl ether. Acetic acid (1.5 ml) was added to the aqueous phase and the mixture was extracted with dichloromethane (50 ml). The organic extract was dried ($MgSO_4$), and the solvent was evaporated in vacuo. The residue was dissolved in a mixture of acetone and diethyl ether and treated with hydrochloric acid in diethyl ether. This afforded 0.35 g of the title compound.

M.p. 201–216° C. Calculated for $C_{24}H_{30}N_2O_2$, HCl, $H_2O$: C, 66.57%; H, 7.68%; N, 6.47%; Cl, 8.19% Found: C, 66.80%; H, 7.30%; N, 6.54%; Cl, 8.31%.

Example 4

1-(4-(10,11-Dihydro-5H-dibenzo[b,f]azepin-5-yl)-(2Z)-butenyl)-(3R)-piperidinecarboxylic Acid Hydrochloride

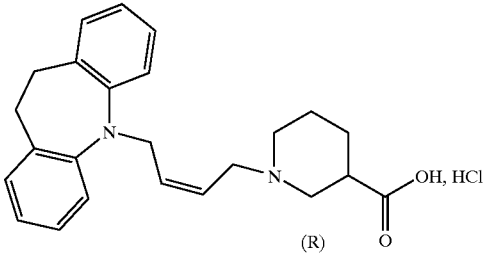

To a solution of iminodibenzyl (6.0 g, 0.03 mol) in dry N,N-dimethylformamide (150 ml) kept under an atmosphere of nitrogen, sodium hydride (1.8 g, 0.045 mol, 60% dispersion in oil) was added in portions. The mixture was stirred for 45 minutes at room temperature, transferred to an addition funnel and slowly added dropwise over 2–3 h to a solution of 1,4-dichloro-2-butene (11.3 g, 0.09 mol) in dry N,N-dimethylformamide (30 ml). The reaction mixture was stirred for 1.5 h at room temperature and heated at 50° C. overnight. After cooling, the mixture was filtered and evaporated. The residue was purified by column chromatography on silica gel (600 ml) using a mixture of ethyl acetate and heptane (1:9) as eluent. This afforded 1.32 g (15%) of 5-(4-chloro-(2Z)-butenyl)-10,11-dihydro-5H-dibenzo[b,f]azepine as an oil.

TLC: $R_f$=0.43 ($SiO_2$:ethyl acetate/heptane=1:9).

Potassium iodide (10.0 g, 0.06 mol) was suspended in methyl ethyl ketone (160 ml) and heated at reflux temperature for 1 h. The above chloride (1.3 g, 0.0046 mol) was dissolved in methyl ethyl ketone (20 ml) and added. The resulting mixture was heated at reflux temperature for 3.5 h. (R)-3-Piperidinecarboxylic acid ethyl ester tartrate (2.1 g, 0.007 mol) and potassium carbonate (1.6 g, 0.012 mol) were added, and the reaction mixture was heated at reflux temperature for 48 h. After cooling, the mixture was filtered (hyflo) and evaporated. The residue was purified by chromatography on silica gel (200 ml) using a mixture of ethyl acetate and heptane (1:1) as eluent. This afforded 0.2 g (10%) of 1-(4-(10,11-dihydro-5H-dibenzo[b,f]azepin-5-yl)-(2Z)-butenyl)-(3R)-piperidinecarboxylic acid ethyl ester as an oil.

TLC: $R_f$=0.13 ($SiO_2$:ethyl acetate/heptane=1:9).

The above ethyl ester (0.2 g, 0.5 mmol) was dissolved in ethanol (4 ml). Sodium hydroxide (0.2 g, 5 mmol) dissolved in water (2 ml) was added, and the reaction mixture was stirred for 2 h at room temperature. Concentrated hydrochloric acid (0.4 ml) was added, followed by dichloromethane (100 ml), and the phases were separated. The aqueous phase was extracted with dichloromethane (2×75 ml), and the combined organic phases were dried ($MgSO_4$) and evaporated. The residue was dissolved in acetone and reevaporated. Isopropyl acetate was added, and the solid precipitate was filtered off, washed with isopropyl acetate and dried to give 24 mg (12%) of the title compound.

HPLC retention time=21.38 minutes (5 μm C18 4×250 mm column, eluting with a 20–80% gradient of 0.1% trifluoroacetic acid/acetonitrile and 0.1% trifluoroacetic acid/water over 30 minutes at 35° C.). $^1$H NMR (400 MHz, DMSO-$d_6$): $\delta_H$ 3.10 (m, 6H); 4.38 (m, 2H); 5.45 (m, 2H); 6.88 (m, 2H); 7.10 (m, 6H).

Example 5

1-(3-(10,11-Dihydro-5H-dibenzo[a,d]cyclohepten-5-ylidene)-1-propionyl)-(3R)-piperidinecarboxylic Acid

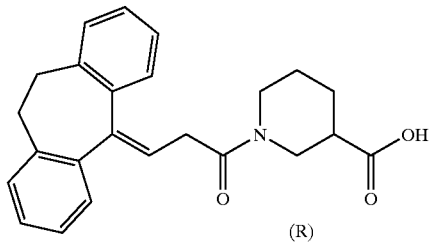

To a solution of (R)-3-piperidinecarboxylic acid ethyl ester (3.14 g, 0.02 mol) in benzene (6 ml), a solution of 3-(10,11-dihydro-5H-dibenzo[a,d]cyclohepten-5-ylidene)-1-propionyl chloride (2.83 g, 0.01 mol, prepared similarly as described in Coll. Czech. Chem. Comm., 52, 1566, 1987) in benzene (8 ml) was added dropwise. When addition was complete, the reaction mixture was stirred for 3 h. Water (15 ml) was added and the phases were separated. The organic phase was dried (MgSO$_4$) and the solvent was evaporated in vacuo. The residue was purified by chromatography on silica gel (100 g) using first benzene and then chloroform as eluents to give 3.9 g (97%) of 1-(3-(10,11-dihydro-5H-dibenzo[a,d]cyclo-hepten-5-ylidene)-1-propionyl)-(3R)-piperidinecarboxylic acid ethyl ester as an oil.

The above ester (3.8 g, 0.0094 mmol) was dissolved in ethanol (20 ml), 15% sodium hydroxide (5 ml) was added, and the reaction mixture was stirred at room temperature for 2.5 h. Benzene (80 ml) was added, and a 2 M solution of tartaric acid in water was added until acidic reaction (pH 2). The benzene solution was washed with water (20 ml), dried over MgSO$_4$ and evaporated in vacuo. The oily residue was stirred with 80 ml of hexane, affording 3.4 g (96%) of the title compound as an amorphous solid.

M.p. 71–76° C. Calculated for C$_{24}$H$_{25}$NO$_3$, 0.1 C$_6$H$_8$: C, 76.93%; H, 6.93%; N, 3.65%; Found: C, 77.08%; H, 7.25%; N, 3.27%.

Example 6

1-(2-(10,11-Dihydro-5H-dibenzo[a,d]cyclohepten-5-yl)-1-ethyl)-(3R)-piperidinecarboxylic Acid Hydrochloride

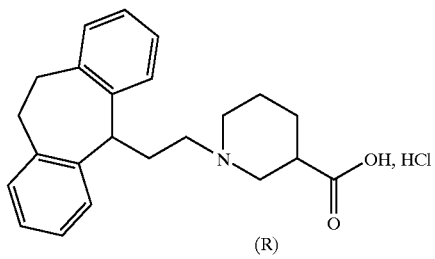

To a solution of 2-(10,11-dihydro-5H-dibenzo[a,d]cyclohepten-5-yl)ethanol (3.6 g, 15 mmol, prepared as described in J. Med. Chem., 1967, 10, 627–637) in toluene (100 ml), triethylamine (4.5 g, 45 mmol) and methanesulfonyl chloride (2.3 g, 20 mmol) were added, and the reaction mixture was stirred at room temperature for 3 h. The reaction mixture was washed three times with water (50 ml), dried (MgSO$_4$), and the solvent was evaporated in vacuo. The residue was dissolved in N,N-dimethylformamide (50 ml) and added to a suspension of (R)-3-piperidinecarboxylic acid ethyl ester tartrate (6.9 g, 22.5 mmol) and potassium carbonate (6.2 g, 45 mmol) in N,N-dimethylformamide (50 ml). The reaction mixture was stirred for 22 h at 50° C., cooled, diluted with benzene (150 ml) and washed with water (3×50 ml). The organic phase was dried (K$_2$CO$_3$) and the solvent was evaporated in vacuo. The residue was purified by column chromatography on silica gel (60 g) using first benzene and then chloroform as eluents. This afforded 3.46 g (51%) of 1-(2-(10,11-dihydro-5H-dibenzo[a,d]cyclohepten-5-yl)-1-ethyl)-(3R)-piperidinecarboxylic acid ethyl ester, which was transformed into its corresponding hydrogen oxalate and crystallised from 2-propanol. Yield 2.8 g (40%).

The above ester hydrogen oxalate (2.53 g, 5.41 mmol) was dissolved in ethanol (30 ml) and a solution of 5 N sodium hydroxide was added (10 ml). The mixture was stirred for 6 h at room temperature. Dichloromethane (350 ml) was added, followed by 2.5 N hydrochloric acid (20 ml). The phases were separated, the organic phase dried (MgSO$_4$) and the solvent was evaporated in vacuo. The residue was reevaporated twice with acetone, and the solid was triturated with a mixture of acetone and diethyl ether (1:1). This afforded after drying 1.8 g (92%) of the title compound.

M.p. 224–227° C. Calculated for C$_{23}$H$_{27}$NO$_2$, HCl: C, 71.58%; H, 7.31%; Cl, 9.18; N, 3.63%; Found: C, 71.51%; H, 7.33%; Cl, 9.19; N, 3.63%.

Example 7

1-(4-(10,11-Dihydro-5H-dibenzo[b,f]azepin-5-yl)-(2E)-butenyl)-(3R)-piperidinecarboxylic Acid Hydrochloride

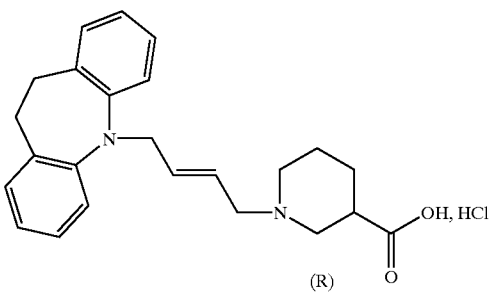

To a solution of iminodibenzyl (7.6 g, 0.039 mol) in dry N,N-dimethylformamide (200 ml) kept under an atmosphere of nitrogen, sodium hydride (2.3 g, 0.058 mol, 60% dispersion in oil) was added in two portions. The mixture was stirred for 3 h at room temperature. (E)-1,4-Dibromo-2-butene (25.0 g, 0.12 mol) in dry N,N-dimethylformamide (60 ml) was added over 1 h. The reaction mixture was heated at 50° C. overnight. After cooling, the mixture was filtered and the solvent evaporated. The residue was purified by column chromatography on silica gel (1700 ml) using a mixture of ethyl acetate and heptane (1:9) as eluent. This afforded crude 5-(4-bromo-(2E)-butenyl)-10,11-dihydro-5H-dibenzo[b,f]azepine as an oil.

TLC: R$_f$=0.42 (SiO$_2$:ethyl acetate/heptane=1:9).

The above bromide (2.9 g, 0.010 mol) was dissolved in methyl ethyl ketone (250 ml). Potassium iodide (3.45 g, 0.02 mol) was added, followed by (R)-3-piperidinecarboxylic acid ethyl ester tartrate (9.29 g, 0.031 mol) and potassium carbonate (5.0 g, 0.04 mol), and the reaction mixture was heated at reflux temperature for 48 h. After cooling, the mixture was filtered (hyflo) and the solvent evaporated. The residue was purified by chromatography on silica gel (1000 ml) using ethyl acetate as eluent. This afforded 0.37 g (9%) of 1-(4-(10,11-dihydro-5H-dibenz[b,f]azepin-5-yl)-(2E)-butenyl)-(3R)-piperidinecarboxylic acid ethyl ester as an oil.

TLC: $R_f$=0.22 (SiO$_2$:ethyl acetate).

The above ethyl ester (0.35 g, 0.87 mmol) was dissolved in ethanol (5 ml). Sodium hydroxide (0.23 g, 6 mmol) was dissolved in water (1 ml) and added, and the reaction mixture was stirred for 1 h at room temperature. 1 N Hydrochloric acid (7 ml) was added, and the mixture was extracted with dichloromethane (2×20 ml. The combined organic phases were washed with brine (20 ml), dried (MgSO$_4$) and evaporated. The residue was dissolved in acetone (10 ml), and the solid precipitate was filtered off and dried to give 0.23 g (66%) of the title compound.

HPLC retention time=20.95 minutes (5 µm C18 4×250 mm column, eluting with a 20–80% gradient of 0.1% trifluoroacetic acid/acetonitrile and 0.1% trifluoroacetic acid/water over 30 minutes at 35° C.). Calculated for C$_{24}$H$_{28}$N$_2$O$_2$, HCl, 0.25 H$_2$O, 0.25 C$_3$H$_6$O$_2$: C, 68.81%; H, 7.23%; N, 6.48%; Found: C, 68.52%; H, 7.35%; N, 6.13%.

Example 8

(R)-1-(3-(10,11-Dihydro-5H-dibenzo[b,f]azepin-5-yl)-3-oxopropyl)-3-piperidinecarboxylic Acid Hydrochloride

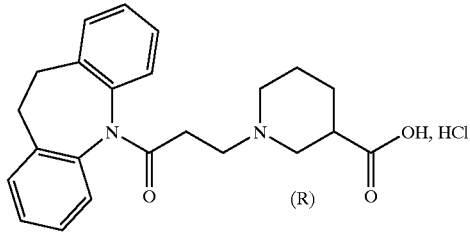

To a solution of iminodibenzyl (10.0 g, 0.051 mol) in toluene (50 ml), 3-chloropropionyl chloride (7.8 g, 0.061 mol) was slowly added drop-wise. The mixture was heated at 95° C. for 30 minutes and left stirring at room temperature overnight. 0.2 N Sodium hydroxide (25 ml) was added and the phases were separated. Toluene (100 ml) was added, and the organic phase was washed with 0.2 N sodium hydroxide (2×25 ml). The organic phase was washed with water (3×33 ml) and brine (30 ml), dried (MgSO$_4$) and evaporated to give crude 3-chloro-1-(10,11-dihydro-5H-dibenzo[b,f]azepin-5-yl)-1-propanone in quantitative yield.

Potassium iodide (10.0 g, 0.060 mol) was suspended in methyl ethyl ketone (180 ml) and heated at reflux temperature for 1.25 h. The above crude chloride (6.46 g) was dissolved in methyl ethyl ketone (20 ml) and added, and under a nitrogen atmosphere, heating at reflux temperature was continued for 2 h. (R)-3-Piperidinecarboxylic acid ethyl ester tartrate (7.87 g, 0.026 mol) and potassium carbonate (6.04 g, 0.044 mol) were added, and the reaction mixture was heated at reflux temperature for an additional 48 h. After cooling, the mixture was filtered (hyflo) and the solvent evaporated. The residue was purified by chromatography on silica gel (600 ml) using a mixture of ethyl acetate and heptane (1:1) as eluent. This afforded 3.32 g (48%) of (R)-1-(3-(10,11-dihydro-5H-dibenz[b,f]azepin-5-yl)-3-oxopropyl)-3-piperidinecarboxylic acid ethyl ester as an oil.

TLC: $R_f$=0.07 (SiO$_2$:ethyl acetate/heptane=1:1).

The above ethyl ester (2.54 g, 0.0062 mol) was dissolved in ethanol (20 ml). Sodium hydroxide (0.9 g) dissolved in water (3.6 ml) was added and the reaction mixture was stirred for 2 h at room temperature. Concentrated hydrochloric acid (3 ml) was added and the mixture was extracted with dichloromethane (200 ml). The organic phase was washed with water (100 ml), dried (MgSO$_4$) and evaporated. Acetone and dichloromethane were added, and the solid precipitate was filtered off and dried, affording 0.99 g (24%) of the title compound.

M.p. 180–183° C. Calculated for C$_{23}$H$_{26}$N$_2$O$_3$, HCl, H$_2$O: C, 63.82%; H, 6.71%; N, 6.47%; Found: C, 63.91%; H, 6.61%; N, 6.23%.

Example 9

(R)-1-(4-(10,11-Dihydro-5H-dibenzo[a,d]cyclohepten-5-yl)-benzyl)-3-piperidinecarboxylic Acid Hydrochloride

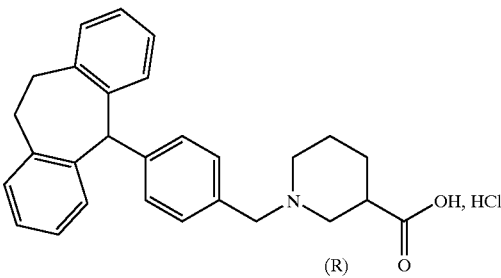

A mixture of magnesium turnings (1.07 g, 0.044 mol) activated with iodine, 1,2-dibromoethane and tetrahydrofuran (40 ml) was kept under a nitrogen atmosphere, and a solution of 4-bromophenylmethyl tetrahydro-2-pyranyl ether (11.20 g, 0.041 mol) in tetrahydrofuran (40 ml) was added dropwise under stirring. The mixture was gently heated to reflux temperature, and heating was continued for 3 h. The mixture was cooled to room temperature, and a solution of 10,11-dihydro-5H-dibenzo[a,d]cyclohepten-5-one (6.86 g, 0.033 mol) in tetrahydrofuran (40 ml) was added dropwise. The mixture was heated at reflux temperature for 1 h, cooled and then poured into an ice-cold saturated solution of ammonium chloride (85 ml). The mixture was extracted with ether (120 ml and 2×70 ml), and the combined organic layers were washed with water (2×40 ml), brine (40 ml) and dried (MgSO$_4$). The solvent was removed in vacuo and the oily residue (14.7 g) was purified by column chromatography on silica gel (200 g) using first benzene and then a mixture of dichloromethane and ethanol (9:1) as eluents. The dichloromethane/ethanol fraction afforded 5.5 g (41%) of 5-(4-(2-tetrahydropyranyloxymethyl)phenyl)-10,11-dihydro-5H-dibenzo[a,d]-cyclohepten-5-ol.

TLC: $R_f$=0.30 (SiO$_2$:chloroform).

A mixture of the above alcohol (5.45 g, 0.014 mol), acetic acid (15 ml), 57% hydroiodic acid (15 ml) and red phosphorus (1.85 g, 0.06 mol) was heated at reflux temperature for 4.5 h. The acidic layer (A) was decanted from the slurry (B) which was diluted with benzene (40 ml). Extraction of acid layer (A) with benzene afforded only 0.25 g of a mixture of compounds. Undissolved phosphorus from mixture (B) was filtered off, washed with additional benzene (10 ml), and the combined organic layers were washed with water (20 ml) and dried (MgSO$_4$). The solvent was evaporated in vacuo, and the resulting residue (6.75 g) was purified by gradient column chromatography on silica gel (150 g) using cyclohexane, chloroform and benzene as eluents. After evaporation of the cyclohexane/benzene (1:1) fraction and washing of the precipitate with cyclohexane, 2.04 g (37%) of 4-(10,11-dihydro-5H-dibenzo[a,d]-cyclohepten-5-yl)phenylmethyliodide was obtained.

TLC: R$_f$=0.69 (SiO$_2$:benzene).

A mixture of the above iodide (1.80 g, 0.0044 mol), (R)-3-piperidinecarboxylic acid ethyl ester (0.69 g, 0.0044 mol) and anhydrous potassium carbonate (1.82 g, 0.0132 mol) in 2-butanone (30 ml) was heated to 50° C. for 6 h. After cooling, the mixture was diluted with ether (50 ml) and water (50 ml) and the phases were separated. The organic phase was washed with water (30 ml) and dried (MgSO$_4$). The solvent was evaporated in vacuo and the oily residue (2.1 g) was purified by gradient column chromatography on silica gel (40 g) using benzene and ethyl acetate as eluents. The benzene/ethyl acetate (9:1) fraction afforded 1.50 g (77%) of (R)-1-(4-(10,11-dihydro-5H-dibenzo[a,d]cyclohepten-5-yl)-benzyl)-3-piperidinecarboxylic acid ethyl ester.

TLC: R$_f$=0.61 (SiO$_2$:chloroform saturated with ammonia/ethanol=100:1).

A mixture of the above ester (1.35 g, 0.003 mol) and 20% sodium hydroxide (0.6 ml) in ethanol (15 ml) was stirred at room temperature for 15 h. After evaporation in vacuo, the residue was diluted with dichloromethane (100 ml), the mixture was neutralised with concentrated acetic acid, washed with water (3×10 ml) and dried (MgSO$_4$). The solvent was evaporated in vacuo and the oily residue (2.2 g) was suspended in ether (20 ml). By drop-wise addition of a solution of hydrogen chloride in ether, the mixture was acidified. The solvent was evaporated in vacuo and the residue was dissolved in acetone (10 ml). Ether (20 ml) was added and the precipitated amorphous solid was filtered off. The solid was redissolved in acetone and ether was added. The separated solid was filtered off and dried. This afforded 1.1 g (80%) of the title compound.

M.p. 167–175° C. Calculated for C$_{28}$H$_{29}$NO$_2$, HCl, 0.75 C$_2$H$_5$OH: C, 73.42%; H, 7.21%; Cl, 7.35%; N, 2.90%; Found: C, 73.41%; H, 6.93%; Cl, 7.34%; N, 2.96%.

Example 10

(R)-1-(4-(10,11-Dihydro-5H-dibenzo[b,f]azepin-5-yl)-2-butyn-1-yl)-3-piperidinecarboxylic Acid

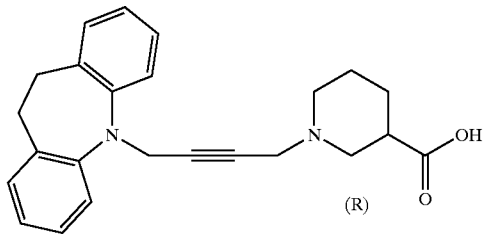

A solution containing 5-propargyl-10,11-dihydro-5H-dibenzo[b,f]azepine (2.45 g, 10.5 mmol, prepared similarly as described in U.S. Pat. No. 3,354,178 (1967)), (R)-3-piperidinecarboxylic acid ethyl ester (1.7 g, 10.8 mmol), paraformaldehyde (0.65 g) and a trace of cuprous chloride in dioxane (25 ml) was heated at reflux temperature for 5 h and left standing overnight. The mixture was filtered and the solvent evaporated. The remaining oil was purified by column chromatography on silica gel (40 g) using chloroform as eluent, affording 3.5 g (83%) of (R)-1-(4-(10,11-dihydro-5H-dibenzo[b,f]azepin-5-yl)-2-butyn-1-yl)-3-piperidinecarboxylic acid ethyl ester.

TLC: R$_f$=0.55 (SiO$_2$:chloroform/ethanol/ammonium hydroxide=20:1:0.1).

The above ester (3.5 g, 8.7 mmol) was dissolved in ethanol (40 ml). 5 N Sodium hydroxide (4 ml) was added and the mixture was allowed to stand for 3 days. Ethanol was evaporated in vacuo and the residue was dissolved in water (50 ml). The solution was washed with diethyl ether (30 ml) and acetic acid (3 ml) was added to the aqueous phase which subsequently was extracted with dichloromethane (50 ml). The organic phase was dried (MgSO$_4$) and the solvent was evaporated in vacuo. The residue was filtered through silica gel (20 g) using ethanol as eluent. The solvent was evaporated and acetone was added to the residue. The solid was isolated by filtration and dried to give 1.8 g (55%) of the title compound.

M.p. 153–154° C. Calculated for C$_{24}$H$_{26}$N$_2$O$_2$, 0.25 H$_2$O: C, 76.06%, H, 7.05%; N, 7.39%; Found: C, 76.39%; H, 7.21%; N, 7.47%.

Example 11

(R)-1-((2R)-Methyl-3-(3-methyl-10,11-dihydro-5H-dibenzo[b,f]azepin-5-yl)-1-propyl)-4-piperidinecarboxylic Acid Hydrochloride

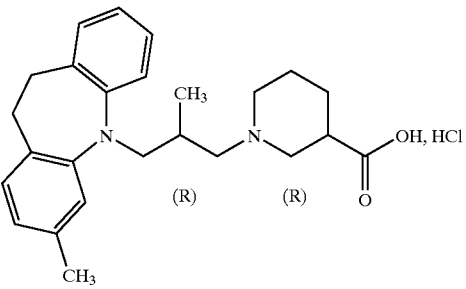

To a solution of 3-methyl-10,11-dihydro-5H-dibenzo[b,f]azepine (4.18 g, 0.02 mol) in benzene (40 ml) a solution of sodium amide (2.03 g, 0.026 mol, 50% suspension in toluene) was added under a nitrogen atmosphere and the mixture was stirred at 75° C. for 1 h. The solution was allowed to cool to 40° C. and 2-(3-Bromo-(2R)-methyl-propoxy)-tetrahydro-pyran (6.16 g, 0.026 mol) was added. The mixture was heated at 75° C. for an additional 19 h. After cooling, water (25 ml) was added and the phases were separated. The aqueous phase was extracted with benzene (2×25 ml). The combined benzene layers were dried (MgSO$_4$) and evaporated. The resulting oily residue was dissolved in methanol (40 ml) and 6 N hydrochloric acid (15 ml) was added. The mixture was heated to gentle reflux for 0.5 h. Methanol was evaporated in vacuo and dichloromethane (100 ml) was added (part of the solid remained undissolved in the flask). The solution was washed with water (20 ml), dried (MgSO$_4$) and the solvent was evaporated. The residue (6.27 g) was purified by column chromatography on silica gel (100 g) using benzene and a mixture of benzene and ethyl acetate (9:1) as eluents. The benzene/ ethyl acetate fraction afforded 1.75 g (31%) of 3-(3-methyl-10,11-dihydro-5H-dibenzo[b,f]azepin-5-yl)-(2S)-methylpropanol.

TLC: $R_f$=0.28 (SiO$_2$:chloroform).

To a solution of the above alcohol (1.70 g, 0.006 mol) and triethylamine (1.82 g, 0.018 mol) in benzene (25 ml), a solution of methanesulfonyl chloride (0.83 g, 0.007 mol) in benzene (5 ml) was added dropwise under cooling with tap water. The solution was allowed to warm to room temperature and was then stirred for 4 h. Separated triethylamine hydrochloride was filtered off and washed with benzene. The combined filtrates were washed with water (2×20 ml) and brine (10 ml) and dried (MgSO$_4$). The solvent was removed in vacuo and the oily residue was dissolved in 2-butanone (30 ml). 4-Piperidine carboxylic acid ethyl ester (0.70 g, 0.0044 mol), potassium iodide (0.74 g, 0.044 mol) and potassium carbonate (1.82, 0.0132 mol) were added, and the mixture was heated at reflux temperature for 11 h. The reaction mixture was cooled and diluted with ether (50 ml) and water (50 ml). The organic layer was separated, washed with water (50 ml) and dried (MgSO$_4$). After evaporation, the residue was purified by gradient column chromatography on silica gel (35 g) using benzene and ethyl acetate as eluents. The benzene/ethyl acetate (10:1) fraction afforded 1.15 g (62%) of (R)-1-((2R)-methyl-3-(3-methyl-10,11-dihydro-5H-dibenzo[b,f]azepin-5-yl)propyl)-4-piperidinecarboxylic acid ethyl ester (1.15 g, 62%) as an oil.

TLC: $R_f$=0.25 (SiO$_2$:chloroform saturated with ammonia/ethanol=60:1).

The above ester (1.1 g, 0.0026 mol) was dissolved in ethanol (10 ml), 20% sodium hydroxide (1.2 ml) was added and the mixture was stirred for 7 h and then left to stand overnight. Ethanol was evaporated in vacuo and the residue was dissolved in dichloromethane (100 ml). The mixture was neutralised with acetic acid, washed with water (2×10 ml) and dried (MgSO$_4$). The solvent was evaporated in vacuo and the residue was suspended in dry ether (20 ml). The mixture was acidified with a solution of hydrogen chloride in ether (pH 1) and then stirred for 15 minutes. Ether was evaporated in vacuo and the residue was stripped with acetone (10 ml). The solid was stirred with acetone (10 ml), filtered off and dried in vacuo. This afforded 0.51 g (45%) of the title compound.

M.p. 216–221° C. Calculated for C$_{25}$H$_{32}$N$_2$O$_2$, HCl, 0.25 H$_2$O: C, 69.27%; H, 7.79%; Cl, 8.18%; N, 6.46%; Found: C, 68.98%; H, 7.63%; Cl, 8.39%; N, 6.29%.

Example 12

(R)-1-(3-(10,11-Dihydro-5H-dibenzo[b,f]azepin-5-yl)1-methylpropyl)-3-piperidinecarboxylic Acid Hydrochloride

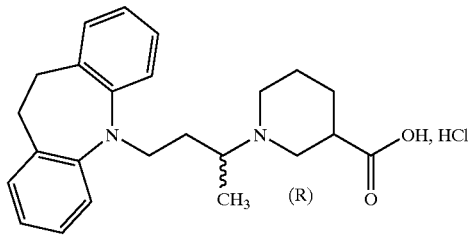

To 4-bromo-2-butanol (8.45 g, 0.055 mol, prepared in two steps starting from 4-hydroxy-2-butanone and hydrogen bromide, followed by reduction of the resulting product with sodium borohydride similarly as described in Zh.Ob-sch.Chim. 1964, 34, 3092 and Tetrahedron 1975, 31, 1251), 3,4-dihydro-2H-pyran (5.11 g, 0.060 mol) was added under stirring. The solution turned dark initially, but decolourised quickly while a highly exothermic reaction proceeded. The reaction mixture was stirred for an additional 3 h and then left to evaporate in vacuo for 0.5 h at 30° C. This afforded 13 g (99%) of crude 2-(3-bromo-1-methyl-propoxy)-tetrahydro-pyran.

To a solution of 10,11-dihydro-5H-dibenzo[b,f]azepine (8.26 g, 0.042 mol) in benzene (100 ml), sodium amide in toluene (4.27 g, 0.055 mol, 50% suspension) was added and the reaction mixture was stirred at 75–80° C. under a nitrogen atmosphere for 1 h. After a short while, a solid was formed in the reaction mixture. The mixture was cooled slightly, the above 2-(3-bromo-1-methyl-propoxy)-tetrahydro-pyran (13 g, 0.055 mol) was added and heating was continued for an additional 20 h. After cooling, water (45 ml) was added and the phases were separated. The aqueous phase was extracted with benzene (20 ml) and the combined benzene extracts were washed with water (20 ml) and dried (MgSO$_4$). The solvent was evaporated in vacuo and the residue (17.5 g) was dissolved in methanol (85 ml). 6 N Hydrochloric acid (30 ml) was added and the mixture was heated at gentle reflux for 0.5 h and subsequently cooled. Methanol was evaporated in vacuo and the residue was dissolved in dichloromethane (150 ml). The organic solution was washed with water (2×20 ml) and dried (MgSO$_4$) and the solvent was evaporated. The residue (11.8 g) was purified by column chromatography on silica gel (150 g) using a mixture of benzene and ethyl acetate (10:1) as eluent. This afforded 9.38 g (83%) 4-(10,11-dihydro-5H-dibenzo[b,f]azepin-5-yl)butan-2-ol after crystallisation from cyclohexane.

TLC: $R_f$=0.25 (SiO$_2$:cyclohexane/ethyl acetate=5:1).

To a solution cooled to 15° C. of the above alcohol (8.50 g, 0.032 mol) and triethylamine (9.71 g, 0.096 mol) in benzene (125 ml), a solution of methanesulfonyl chloride (4.40 g, 0.096 mol) in benzene (30 ml) was added drop-wise under stirring and tap water cooling. After the addition was complete the reaction mixture was allowed to warm up to room temperature and stirred for an additional 2 h. Precipitated triethylamine hydrochloride was filtered off and washed with benzene (30 ml). The organic filtrate was washed with water (2×100 ml), brine (80 ml), and dried (MgSO$_4$). The solvent was evaporated in vacuo and the residual oil (11.05 g) solidified after addition of cyclohexane (30 ml). The precipitate was filtered off and washed with cyclohexane (50 ml) and dried at room temperature. This reaction afforded 8.58 g (77%) of methanesulfonic acid 3-(10,11-dihydro-dibenzo[b,f]azepin-5-yl)-1-methyl-propyl ester.

A mixture of above methanesulfonate (3.45 g, 0.01 mol), (R)-3-piperidinecarboxylic acid ethyl ester tartrate (3.07 g, 0.01 mol), potassium carbonate (5.52 g, 0.04 mol) and potassium iodide (1.66 g, 0.01 mol) in 2-butanone (130 ml) was stirred at 70–80° C. for 15 h. After cooling, the mixture was poured into a mixture of water (150 ml) and ether (150 ml) and the layers were separated. The aqueous layer was extracted with ether (50 ml) and the combined organic phases were washed with water (2×50 ml) and dried (MgSO$_4$). After evaporation of the solvent in vacuo the oily residue (4.00 g) was purified by column chromatography on silica gel (100 g) using a mixture of benzene and ethyl acetate (1:1) as eluent. This afforded 1.46 g (30%) of (R)-1-(3-(10,11-dihydro-5H-dibenzo[b,f]azepin-5-yl)1-methylpropyl)-3-piperidinecarboxylic acid ethyl ester as an oil.

TLC: $R_f$=0.30 (SiO$_2$:chloroform saturated with ammonia/ethanol=50:1).

A solution of the above ester (1.35 g, 0.0028 mol) and 20% sodium hydroxide (1.9 ml) in ethanol (16 ml) was stirred for 12 h at room temperature. The solvent was removed in vacuo and the residue dissolved in dichloromethane (150 ml). Subsequently, acetic acid was added to neutralise the solution and the organic solution was washed with water (2×20 ml) and dried (MgSO$_4$). The solvent was removed in vacuo and the oily residue was dissolved in dry ether. An ether solution of hydrogen chloride was added to acidic reaction. The ether was removed in vacuo, and the residue (1.24 g) was stripped with acetone (3×20 ml) and dissolved in acetone (20 ml). The solid was filtered off and washed with acetone. After drying 0.88 g (75%) of the title compound was obtained.

M.p. 214–218° C. Calculated for C$_{24}$H$_{30}$N$_2$O$_2$, HCl, 0.25 H$_2$O: C, 68.71%; H, 7.57%; Cl, 8.45%; N, 6.68%; Found: C, 68.65%; H, 7.56%; Cl, 8.40%; N, 6.50%.

Example 13

(R)-1-(2-(10,11-dihydro-5H-dibenzo[b,f]azepin-5-yl)-1-methyl-ethyl)-3-piperidinecarboxylic Acid Hydrochloride

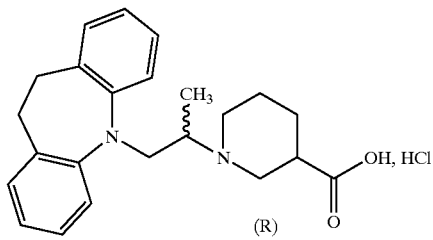

To a mixture of 1-bromo-2-propanol (24.3 g, 0.175 mol, prepared similarly as described in J. Pharm. Soc. Jap. 1955,75,109) and 3,4-dihydro-2H-pyran (14.7 g, 0.175 mol), a saturated solution of hydrogen chloride in ether (4 drops) was added. After the highly exothermic reaction was complete the reaction mixture was stirred at room temperature for 6 h and left to stand overnight. The mixture was evaporated in vacuo (at 35° C.) and the residual crude 2-(2-bromo-1-methyl-ethoxy)-tetrahydro-pyran (39.5 g) was used without further purification.

To a solution of 10,11-dihydro-5H-dibenzo[b,f]azepine (5.86 g, 0.03 mol) in benzene (75 ml) under a nitrogen atmosphere, sodium amide (3.04 g, 0.039 mol, 50% suspension in toluene) was added and the mixture was heated to 70° C. for 1 h. During this time a solid precipitated from the solution. The mixture was partially cooled and the above crude 2-(2-bromo-1-methyl-ethoxy)-tetrahydro-pyran (8.70 g, 0.039 mol) was added. The reaction mixture was heated to 75–80° C. under stirring for 18 h. Under cooling, water was added (30 ml) and the layers were separated. The aqueous phase was extracted with benzene (15 ml). The combined benzene phases were washed with water (10 ml) and dried (MgSO$_4$). After evaporation of the solvent in vacuo the oily residue (11.9 g) was dissolved in methanol (60 ml). 6 N Hydrochloric acid (22 ml) was added and the solution was heated at reflux temperature for 0.5 h. Methanol was evaporated in vacuo and the residue was extracted with dichloromethane (2×100 ml). The combined organic extracts were dried (MgSO$_4$) and the solvent was evaporated. The residue (7.77 g) was purified by column chromatography on silica gel (150 g) using a mixture of benzene and ethyl acetate (10:1) as solvent, This afforded 3.29 g (43%) of 1-(10,11-Dihydro-dibenzo[b,f]azepin-5-yl)-propan-2-ol.

TLC: $R_f$=0.50 (SiO$_2$:chloroform).

To a stirred solution of the above alcohol (3.29 g, 0.013 mol) and triethylamine (3.94 g, 0.039 mol) in benzene (50 ml), a solution of methanesulfonyl chloride (1.86 g, 0.016 mol) in benzene (15 ml) was added drop-wise over 15 minutes at 15° C. The reaction mixture was allowed to warm up to room temperature and stirred for additional 2 h. Separated triethylamine hydrochloride was filtered off, washed with benzene (20 ml), and the combined benzene layers were washed with water (2×50 ml), brine (40 ml), and dried (MgSO$_4$). The solvent was removed in vacuo and the oily residue (3.61 g, 83%) crystallised after standing at room temperature, affording 3.61 g (83%) of methanesulfonic acid 2-(10,11-dihydro-dibenzo[b,f]azepin-5-yl)-1-methyl-ethyl ester.

A mixture of the above crude methanesulfonate (1.20 g, 0.0036 mol), (R)-3-piperidinecarboxylic acid ethyl ester tartrate (1.11 g, 0.0036 mol), potassium carbonate (1.99 g, 0.014 mol) and potassium iodide (0.59 g, 0.0036 mmol) in 2-butanone (35 ml) was heated at 60–70° C. for 19 h. After cooling, the reaction mixture was poured into a mixture of water (50 ml) and ether (50 ml). The layers were separated, and the aqueous phase was extracted with ether (20 ml). The combined organic extracts were washed with water (20 ml) and dried (MgSO$_4$). The residue (1.47 g) was purified by column chromatography on silica gel (35 g) using first benzene and then a mixture of benzene and ethyl acetate (9:1): as eluents. This afforded 0.40 g (28%) of (R)-1-(2-(10,11-dihydro-5H-dibenzo[b,f]azepin-5-yl)-1-methyl-ethyl)-3-piperidinecarboxylic acid ethyl ester.

TLC: $R_f$=0.30 (SiO$_2$:chloroform saturated with ammonia/ethanol=60:1).

A solution of the above ester (0.40 g, 0.001 mol) and 20% sodium hydroxide (0.4 ml) in ethanol (6 ml) was stirred at room temperature for 6 h. Ethanol was evaporated in vacuo and the residue was dissolved in dichloromethane (50 ml). The resulting solution was acidified with acetic acid and the organic layer was separated, washed with water (2×20 ml) and dried (MgSO$_4$). The solvent was evaporated in vacuo and the residual amorphous solid was treated with a solution of hydrogen chloride in ether. The solvent was removed in vacuo and the foamy residue was dissolved in acetone. The title compound was filtered off, washed with acetone (2×10 ml) and dried in vacuo. Yield 0.31 g (76%).

M.p. 213–223° C. Calculated for C$_{23}$H$_{28}$N$_2$O$_2$, HCl, 0.75 H$_2$O: C, 66.67%; H, 7.13%; N, 6.76%; Found: C, 66.56%; H, 7.15%; N, 6.64%.

Example 14

(R)-1-(2-(10,11-Dihydro-5H-dibenzo[a,d]
cyclohepten-5-ylidene)-1-propyl)-3-
piperidinecarboxylic Acid Hydrochloride

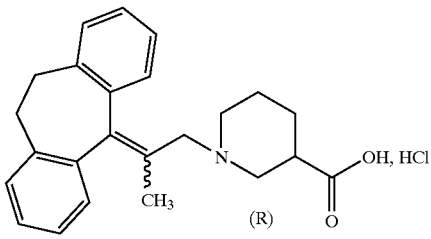

A solution of methoxymethyl magnesiumchloride in dry tetrahydrofuran (prepared from methoxymethyl chloride (16.1 g, 0.2 mol), magnesium turnings (4.8 g, 0.2 mol), mercury chloride (0.25 g) and dry tetrahydrofuran (30 ml)) was cooled on an ice-salt bath to −10° C. A solution of 5-acetyl-10,11-dihydro-5H-dibenzo[a,d]cycloheptene (21.4 g, 0.09 mol, prepared as described in Belg., 609, 095, 1962) in dry tetrahydrofuran (50 ml) was added drop-wise. When addition was complete the mixture was stirred for 1 h. Saturated ammonium chloride (150 ml) was carefully added and the mixture was extracted with diethyl ether (2×100 ml). The combined extracts were dried (MgSO$_4$) and the solvent was evaporated in vacuo to give a residue which was fractionally distilled. The fraction collected at b.p. 130–140° C./70 Pa was purified by gradient column chromatography on silica gel (80 g) using cyclohexane and then benzene as eluents. The benzene fraction afforded 9.4 g of crude 5-(1-methoxymethylethylidene)-10,11-dihydro-5H-dibenzo[a,d]cycloheptene as an oil.

TLC: R$_f$=0.15 (SiO$_2$:benzene).

The above ether (3.6 g, 13.6 mmol) was dissolved in acetic acid (40 ml) and 48% hydrobromic acid (20 ml) was added. After 7 days the mixture was diluted with water (200 ml) and extracted with benzene (100 ml). The organic phase was dried (MgSO$_4$), filtered and the solvent was evaporated in vacuo to give 3.8 g of crude 5-(1-methyl-2-bromoethylidene)-10,11-dihydro-5H-dibenzo[a,d]cycloheptene.

A mixture of the above crude bromide (3.8 g), (R)-3-piperidinecarboxylic acid ethyl ester tartrate (3.6 g, 12 mmol), potassium carbonate (6.3 g, 45.6 mmol) and acetone (100 ml) was heated at reflux temperature for 14 h. The mixture was filtered and the solvent evaporated in vacuo. The residue was purified by gradient column chromatography on silica gel (40 g) using benzene and then chloroform as eluents. The chloroform fraction afforded 0.94 g (18%) of (R)-1-(2-(10,11-dihydro-5H-dibenzo[a,d]cyclohepten-5-ylidene)-1-propyl)-3-piperidinecarboxylic acid ethyl ester as an oil.

TLC: R$_f$=0.60 (SiO$_2$:chloroform/ethanol/ammonium hydroxide=20:1:0.05).

The above ester (0.94 g, 2.4 mmol) was dissolved in ethanol (20 ml) and 5 N sodium hydroxide (2 ml) was added. The mixture was stirred at room temperature for 2 days and ethanol was evaporated in vacuo. Water (20 ml) was added and the mixture was extracted with diethyl ether. Acetic acid (1.5 ml) was added to the aqueous phase and the mixture was extracted with dichloromethane (50 ml). The organic extract was dried (MgSO$_4$) and the solvent was evaporated in vacuo. The residue was dissolved in diethyl ether and treated with hydrochloric acid. The precipitate was filtered off and dried to give 0.67 g (77%) of the title compound as a solid.

M.p. 151–155° C. Calculated for C$_{24}$H$_{27}$NO$_2$, HCl, 1.25 H$_2$O: C, 70.06%; H, 7.23%; Cl, 8.62%; N, 3.40%; Found: C, 69.94%; H, 7.26%; Cl, 8.77%; N, 3.22%.

Example 15

(R)-1-(10,11-Dihydro-5H-dibenzo[a,d]cyclohepten-
5-yl)methyl)-3-piperidinecarboxylic Acid
Hydrochloride

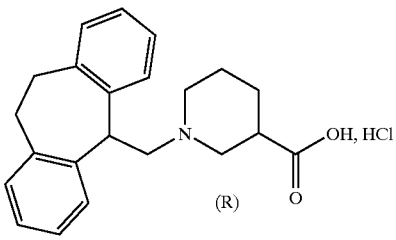

Sodium cyano borohydride (314 mg, 5 mmol) was dissolved in dry methanol (6 ml) and added dropwise under stirring to a mixture of 10,11-dihydro-5H-dibenzo[a,d]cyclohepten-5-ylmethanal (1.11 g, 5 mmol, prepared similarly as described in Ger. Offen 2,106 165, 1971, CA 75, 129 687), (R)-3-piperidinecarboxylic acid ethyl ester (1.57 g, 10 mmol) and zinc chloride (0.34 g, 2.5 mmol) in dry methanol (15 ml) over 30 minutes at 25° C. The reaction mixture was stirred at room temperature for 3 h and left to stand overnight. The methanol was evaporated in vacuo and benzene (30 ml) and 1.2 N sodium bicarbonate (15 ml) were added. The phases were separated and the organic phase was washed with water (30 ml) and brine (2×30 ml) and dried (sodium sulfate). The solvent was evaporated in vacuo and the oily residue (1.68 g) was purified by column chromatography on silica gel (35 g) using benzene as eluent. This afforded 1.12 g (62%) of (R)-1-((10,11-dihydro-5H-dibenzo[a,d]cyclohepten-5-yl)methyl)-3-piperidinecarboxylic acid ethyl ester.

TLC: R$_f$=0.54 (SiO$_2$:chloroform/methanol=30:1).

To a stirred solution of the above ethyl ester (1.12 g, 3.1 mmol) in 96% ethanol (11 ml), sodium hydroxide (7.5 ml) was added dropwise at 25° C. over 15 minutes. After stirring for 1 h the reaction mixture was left to stand at room temperature overnight. Dichloromethane (200 ml) was added and the mixture was acidified with 3 N hydrochloric acid (10 ml) to pH 1. The organic layer was separated and dried (sodium sulfate). The solvent was evaporated in vacuo and the residue was re-evaporated with acetone (30 ml). The solid residue was triturated with a mixture of acetone and ether (2:3) (2×10 ml) and subsequently with ether (2×10 ml) to give 990 mg (86%) of the title compound.

M.p. 254–256° C. Calculated for C$_{22}$H$_{25}$NO$_2$, HCl, 0.5 H$_2$O: C, 69.39%; H, 7.14%; N, 3.68%; Found: C, 69.35%; H, 6.95%; N, 3.83%.

Example 16

1-(3-(10,11-Dihydro-5H-dibenzo[b,f]azepin-5-yl)-(2R)-methyl-1-propyl)-3-pyrrolidinylacetic Acid Hydrochloride

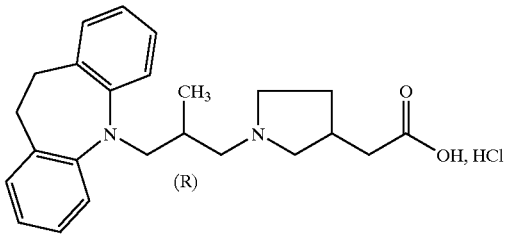

To a solution of 3-(10,11-dihydro-5H-dibenzo[b,f]azepin-5-yl)-(2R)-methyl-1-propanol (1.65 g, 6.18 mmol) in benzene (30 ml), triethylamine (2 ml) was added followed by methanesulfonyl chloride (1.0 g, 8.7 mmol). The reaction mixture was stirred for 6 h, water was added and the phases were separated. The organic phase was dried (MgSO$_4$) and the solvent was evaporated in vacuo. The residue was dissolved in N,N-dimethylformamide (10 ml), and 3-pyrrolidinylacetic acid methyl ester acetate (1.7 g, 8.4 mmol) and potassium carbonate (3.1 g, 22.5 mmol) were added. The mixture was heated at 100° C. for 10 h. Water was added and the mixture was extracted with benzene (50 ml). The organic phase was dried (K$_2$CO$_3$), filtered and the solvent evaporated in vacuo, affording a residue which was purified by column chromatography on silica gel (25 g) using chloroform as eluent. This gave 1.0 g of 1-(3-(10,11-dihydro-5H-dibenzo[b,f]azepin-5-yl)-(2R)-methyl-1-propyl)-3-pyrrolidinylacetic acid methyl ester as an oil.

TLC: R$_f$=0.29 (SiO$_2$:chloroform/ethanol/ammonia= 20:1:0.05).

The above ester (1.0 g, 2.5 mmol) was dissolved in ethanol (20 ml) and 5 N sodium hydroxide (2 ml) was added. The mixture was stirred at room temperature for 7 days and ethanol was evaporated in vacuo. Water (20 ml) was added and the mixture was extracted with diethyl ether. Acetic acid (1.5 ml) was added to the aqueous phase and the mixture was extracted with dichloromethane (50 ml). The organic extract was dried (MgSO$_4$) and the solvent was evaporated in vacuo. The residue was dissolved in a mixture of acetone and diethyl ether and treated with hydrogen chloride in diethyl ether. This gave 0.20 g of the title compound.

M.p. 192–199° C. Calculated for C$_{24}$H$_{30}$N$_2$O$_2$, HCl, 0.25 H$_2$O: C, 68.72%; H, 7.57%; N, 6.68%; Cl, 8.45%; Found: C, 68.38%; H, 7.60%; N, 6.25%; Cl, 8.83%.

Example 17

2-(1-(3-(10,11-Dihydrodibenzo[b,f]azepin-5-yl)-(2R)-methylpropyl)-4-piperazinyl)-nicotinic Acid Dihydrochloride

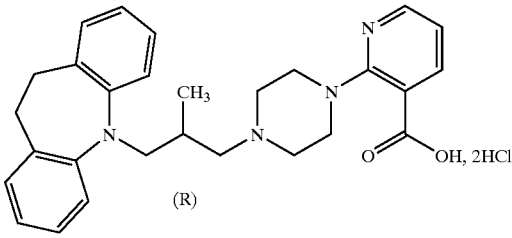

To a solution of 10,11-dihydro-5H-dibenzo[b,f]azepine (2.75 g, 14 mmol) in dry benzene (25 ml), sodium amide (0.55 g, 14 mmol) was added and the mixture was stirred and heated at 80° C. for 1 h. (R)-2-(3-Brom-2-methylpropoxy) tetrahydro-2H-pyran (3.3 g, 14 mmol) was added and stirring and heating was continued for 20 h. After cooling to room temperature, water (10 ml) was added, and the phases were separated. The organic phase was evaporated until dryness. The residue was dissolved in a mixture of methanol (40 ml) and 4 N hydrochloric acid (15 ml). The mixture was heated at reflux temperature for 15 minutes, methanol was evaporated and the residue was extracted with benzene (50 ml). The organic extract was dried (K$_2$CO$_3$), filtered and the solvent evaporated in vacuo. This afforded a residue which was further purified by chromatography on silica gel (40 g) using first chloroform and then ethyl acetate as eluents. This afforded 1.45 g of (R)-3-(10,11-dihydro-5H-dibenzo[b,f] azepin-5-yl)-2-methyl-1-propanol as an oil.

TLC: R$_f$=0.60 (SiO$_2$:benzene/ether/ethanol=10:10:1).

The above alcohol (1.45 g, 5.4 mmol) was dissolved in benzene (25 ml) and triethylamine (1.5 ml) was added. Methanesulfonyl chloride (0.75 g, 6.5 mmol) was added and the reaction mixture was stirred for 6 h. Water was added and the phases were separated. The organic phase was dried (MgSO$_4$) and the solvent was evaporated in vacuo to give a residue which was dissolved in N,N-dimethylformamide (10 ml). To this solution, 2-(1-piperazinyl)-3-pyridinecarboxylic acid ethyl ester (1.23 g, 5.2 mmol) and potassium carbonate (0.75 g, 5.4 mmol) were added and the mixture was stirred and heated at 100° C. for 11 h. The mixture was diluted with water and extracted with benzene (50 ml). The organic phase was dried (K$_2$CO$_3$), filtered and the solvent evaporated in vacuo. The residue was purified by chromatography on silica gel (30 g) using ethyl acetate as eluent. This afforded 0.84 g of 2-(1-(3-(10,11-dihydrodibenzo[b,f]azepin-5-yl)-(2R)-methylpropyl)-4-piperazinyl)-nicotinic acid ethyl ester as an oil.

TLC: R$_f$=0.35 (SiO$_2$:chloroform/ethanol/ammonium hydroxide=20:1:0.1).

The above ester (0.84 g, 2 mmol) was dissolved in ethanol (20 ml) and 5 N sodium hydroxide (2 ml) was added. The mixture was stirred at room temperature for 4 days and ethanol was evaporated in vacuo. Water (20 ml) was added and the mixture was extracted with diethyl ether. Acetic acid (1.5 ml) was added to the aqueous phase and the mixture was extracted with dichloromethane (50 ml). The organic extract was dried (MgSO$_4$) and the solvent was evaporated in vacuo. The residue was dissolved in a mixture of acetone and diethyl ether and treated with hydrochloride in diethyl ether. After isolation, this afforded 0.37 g of the title compound.

M.p. 217–223° C. Calculated for $C_{28}H_{32}N_4O_2$, 2 HCl, 0.5 $H_2O$: C, 62.45%; H, 6.55%; N, 10.40%; Found: C, 62.29%; H, 6.56%; N, 9.99%

Example 18

(R)-1-(2-(10,11-Dihydro-5H-dibenzo[b,f]azepin-5-ylmethyl)-1-pentyl)-3-piperidinecarboxylic Acid Hydrochloride

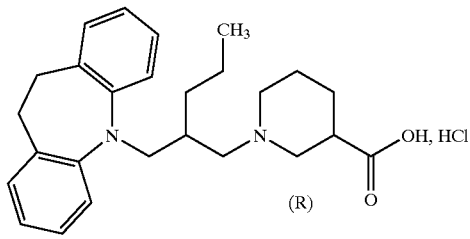

10,11-Dihydro-5H-dibenzo[b,f]azepine (9.4 g, 0.048 mol) was dissolved in dry toluene (200 ml), and under nitrogen, ethyl 2-propylmalonylchloride (11.2 g, 0.058 mol, prepared similarly as described in J. Am. Chem. Soc., 68, 1507, 1946) was slowly added. The reaction mixture was heated at reflux temperature for 2 h and then allowed to cool to room temperature. Under stirring 0.2 N sodium hydroxide (25 ml) and water were added. More toluene (1 l) was added and the phases were separated. The organic phase was washed with water (3×500 ml) and brine (500 ml). After drying ($MgSO_4$) the organic phase was evaporated in vacuo affording the crude amide in quantitative yield.

To a solution of lithium hydride (7.9 g, 0.21 mol) in dry toluene (320 ml) tetrahydrofuran (30 ml) was added under nitrogen. The above amide (16.8 g, 0.048 mol) was dissolved in dry tetrahydrofuran (100 ml) and slowly added at 20–25° C. The reaction mixture was left stirring overnight at room temperature. Water (8 ml) was added drop-wise followed by 4 N sodium hydroxide (8 ml) and finally water (24 ml). The resulting precipitate was filtered off and the toluene solution was dried ($MgSO_4$). The crude product was purified by column chromatography on silica gel (140 g). By elution with first benzene and then with chloroform, 1.45 g (10%) of 2-(10,11-dihydro-5H-dibenzo[b,f]azepin-5-ylmethyl)-1-pentanol was obtained as an oil.

TLC: $R_f$=0.65 ($SiO_2$:benzene/ether/ethanol=10:10:1).

The above alcohol (1.45 g, 4.9 mmol) was dissolved in benzene (50 ml) and triethylamine (2 ml) was added. Methanesulfonyl chloride (0.8 g, 7 mmol) was added and the reaction mixture was stirred for 2 h. Water (50 ml) was added and the phases were separated. The organic phase was dried ($MgSO_4$) and the solvent evaporated in vacuo, affording a residue which was dissolved in N,N-dimethylformamide (10 ml). To this solution (R)-3-piperidine-carboxylic acid ethyl ester tartrate (1.6 g, 5.2 mmol) and potassium carbonate (1.5 g, 10.8 mmol) were added and the mixture was heated at 120° C. for 6 h. Benzene (100 ml) and water (100 ml) were added and the phases were separated. The organic phase was dried ($K_2CO_3$) and the solvent evaporated in vacuo. The residue was purified by column chromatography on silica gel (25 g) using chloroform as eluent. This afforded 1.5 g (70%) of (R)-1-(2-(10,11-dihydro-5H-dibenzo[b,f]azepin-5-ylmethyl)-1-pentyl)-3-piperidinecarboxylic acid ethyl ester as an oil.

TLC: $R_f$=0.40 ($SiO_2$:chloroform/ether=1:1).

The above ester (1.5 g, 3.5 mmol) was dissolved in ethanol (50 ml) and 5 N sodium hydroxide (3 ml) was added. The mixture was stirred at room temperature for 20 h, ethanol was evaporated in vacuo and water (40 ml) was added. The mixture was extracted with diethyl ether (40 ml) and the phases were separated. Acetic acid (3 ml) was added to the aqueous phase and the mixture was extracted with dichloromethane (50 ml). The organic phase was dried ($MgSO_4$) and the solvent was evaporated in vacuo. The residue was dissolved in diethyl ether and treated with hydrochloride in diethyl ether. The precipitate was filtered off and dried to give 1.02 g (65%) of the title compound.

M.p. 116–120° C. Calculated for $C_{26}H34N_2O_2$, HCl, 0.5 $H_2O$: C, 69.08%; H, 8.03%; N, 6.20%; Cl, 7.84%; Found: C, 69.02%; H, 7.84%; N, 5.96%; Cl, 7.39%.

Example 19

2-(4-(3-(10,11-Dihydro-5H-dibenzo[b,d]azepin-5-yl)-2-hydroxypropyl)piperazin-1-yl)nicotinic Acid Hydrochloride

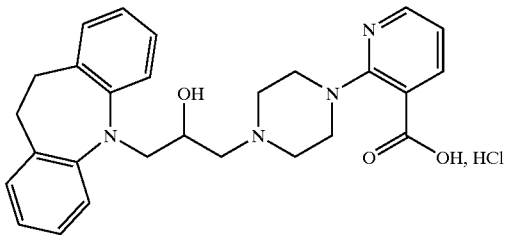

To a solution of 10,11-dihydro-5H-dibenzo[b,f]azepine (5.11 g, 26.2 mmol) in dry benzene (80 ml) sodium amide in toluene (50%, 2.28 g) was added. The mixture was stirred and heated at reflux temperature for 3 h until ammonia evolution had ceased. After cooling to 10° C. under a stream of nitrogen, distilled epichlorohydrin (2.8 ml) was added and the mixture was stirred and heated at 80° C. for 15 h. The dark mixture was then poured onto ice and extracted with diethyl ether (2×125 ml) to give a colourless aqueous layer with a thick beige solid and a brown organic layer. The organic solution was washed with water (100 ml), dried ($MgSO_4$) and evaporated to give 4.73 g of a viscous liquid.

The above crude alcohol (2.54 g), 2-(piperazine-1-yl) nicotinic acid ethyl ester (1.36 g) and 2-butanone (10 ml) were stirred and heated at reflux temperature for 60 h. The reaction mixture was diluted with 2-butanone (5 ml) and finely powdered sodium carbonate (1.32 g) was added. The mixture was stirred for 1.5 h at reflux temperature and filtered. The remaining solid was washed with 2-butanone and diethyl ether and the organic solution was evaporated. This afforded 3.99 g of an amorphous solid, which was purified by column chromatography on silica gel (150 g) using benzene, chloroform, chloroform with ammonia and chloroform with 1% ethanol, respectively as eluents. This afforded 1.63 g (58%) of 2-(4-(3-(10,11-dihydro-5H-dibenzo[b,f]azepin-5-yl)-2-hydroxy)propyl)piperazin-1-yl) nicotinic acid ethyl ester as an oil.

TLC: $R_f$=0.23 ($SiO_2$:ethyl acetate).

The above ester (1.60 g) was dissolved in ethanol (12 ml). Sodium hydroxide (0.6 g) and water (3 ml) were added and the homogeneous mixture was stirred for 16 h. The solution was filtered and diluted with a few ml of ethyl alcohol. Under stirring, concentrated hydrochloric acid was added dropwise to pH 1. The mixture containing a precipitated solid was then poured into dichloromethane (300 ml). The salt dissolved, but on standing after several hours, a new solid precipitated. This was filtered off and washed with dichloromethane. The solid was dried in vacuo at 70° C. to afford 0.975 g of the title compound.

M.p. 125–130° C.

Example 20

1-(3-(10,11-Dihydro-5H-dibenzo[b,f]azepin-5-yl)-2-methyl-3-oxo-propyl)-3-piperidinearboxylic Acid Hemifumarate

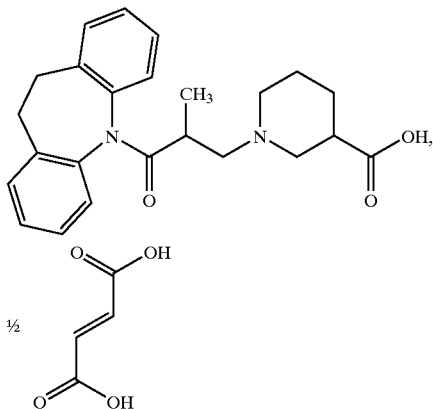

Benzyl methacrylate (29.1 g, 0.165 mol) was added drop-wise under stirring over 30 minutes to 3-piperidine carboxylic acid ethyl ester (20 g, 0.127 mol). Triton B (4 ml) was added and the reaction mixture heated at 70–75° C. for 24 h. After evaporation in vacuo the product was purified by column chromatography on silica gel (480 g) using chloroform and a mixture of chloroform and ethanol (8:2) as eluents. This afforded 16.7 g (39%) of 3-(3-carbethoxypiperidin-1-yl)-2-methylpropionic acid benzyl ester as an oil.

TLC: $R_f$=0.43 (SiO$_2$:chloroform).

The above diester (16.6 g, 0.0498 mol) was dissolved in ethanol (170 ml). Palladium on carbon (Pd 10%, 1.6 g) was added and the mixture was hydrogenated at room temperature and atmospheric pressure. The calculated amount of hydrogen was absorbed in 1 h. The catalyst was filtered off and the filtrate was evaporated in vacuo. This afforded 11.6 g (96%) of 3-(3-carbethoxypiperidin-1-yl)-2-methylpropionic acid as an oil.

Oxalyl chloride (3.8 g, 30 mmol) was added to a solution of the above acid (5.3 g, 21.8 mmol) in dichloromethane (50 ml),. The mixture was allowed to stand at room temperature for 24 h and dichloromethane was evaporated in vacuo. The residue was dissolved in 1,2-dichlorethane (50 ml), 10,11-dihydro-5H-dibenzo[b,f]azepine (4.3 g, 22 mmol) was added and the mixture was heated at reflux temperature for 3 h. After cooling, the mixture was washed with aqueous ammonia, dried (MgSO$_4$) and the solvent evaporated in vacuo. The residue was purified by gradient column chromatography on silica gel (50 g) using benzene and ethyl acetate as eluents. The ethyl acetate fraction afforded 4.0 g (44%) of 1-(3-(10,11-dihydro-dibenzo[b,f]azepin-5-yl)-2-methyl-3-oxo-propyl)-3-piperidinecarboxylic acid ethyl ester as an oil.

TLC: $R_f$=0.20 (SiO$_2$:benzene/diethyl ether=1:1).

The above ester (4.0 g, 9.5 mmol) was dissolved in ethanol (50 ml) and 5 N sodium hydroxide (4 ml) was added. The mixture was allowed to stand for 3 days at room temperature. Ethanol was evaporated in vacuo and water (50 ml) was added. The mixture was extracted with diethyl ether and the phases were separated. Acetic acid (4 ml) was added to the aqueous phase and the mixture was extracted with dichloromethane (5×50 ml). The combined dichloromethane extracts were dried (MgSO$_4$) and the solvent was evaporated in vacuo. The residue was dissolved in diethyl ether and treated with fumaric acid in ethanol affording 3.05 g (70%) of the title compound.

M.p. 181–183° C. Calculated for $C_{24}H_{28}N_2O_3$, 0.5 $C_4H_4O_4$, 0.25 $C_2H_5OH$: C, 68.89%; H, 6.87%; N, 6.06%; Found: C, 68.41%; H, 6.98%; N, 6.05%.

Example 21

(R)-1-(3-(10,11-Dihydro-5H-dibenzo[b,f]azepin-5-yl)-1-propionyl)-3-piperidinecarboxylic Acid

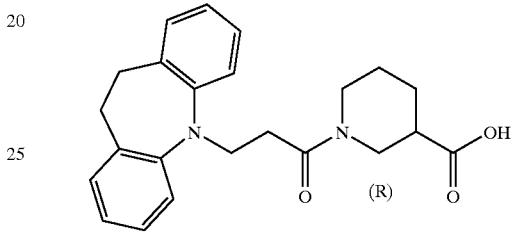

Iminodibenzyl (50.0 g, 0.256 mol) was dissolved in N,N-dimethylformamide (700 ml), sodium hydride (12.3 g, 0.306 mol, 60% dispersion in oil) was slowly added in portions and the mixture was stirred at 50° C. for 2 h. Ethyl 3-bromopropionate (100 ml, 0.77 mol) was slowly added drop-wise and the mixture was heated at reflux temperature overnight. The mixture was cooled and evaporated. The residue was suspended in dichloromethane (150 ml), filtered and the solvent was evaporated. The resulting residue was purified in portions by column chromatography on silica gel using dichloromethane as eluent to give 5.1 g (7%) of 3-(10,11-dihydro-5H-dibenzo[b,f]azepin-5-yl)-1-propionic acid ethyl ester.

TLC: $R_f$=0.69 (SiO$_2$:dichloromethane).

The above ester (1.41 g, 4.77 mmol) was dissolved in ethanol (30 ml) and a solution of sodium hydroxide (0.75 g, 18.8 mmol) in water (5 ml) was added. The mixture was stirred for 3.5 h. 1 N Hydrochloric acid (17 ml) was added and the mixture was extracted with dichloromethane (2×25 ml). The combined organic extracts were washed with brine (50 ml), dried (MgSO$_4$) and the solvent was evaporated to give 1.18 g (92%) of 3-(10,11-dihydro-5H-dibenzo[b,f] azepin-5-yl)-1-propionic acid.

The above acid (1.15 g, 4.3 mmol) was dissolved in dichloromethane (25 ml) and thionylchloride (1.02 g, 8.6 mmol) was added. The mixture was heated at reflux temperature for 2 h and evaporated to give the corresponding acid chloride. This was suspended in acetonitrile (15 ml) and added to a mixture of (R)-3-piperidinecarboxylic acid ethyl ester tartrate (2.6 g, 8.6 mmol), potassium carbonate (2.08 g, 15 mmol) and acetonitrile (10 ml). The reaction mixture was heated at reflux temperature for 45 minutes and the solvent was evaporated. Water (20 ml) was added and the mixture was extracted with dichloromethane (2×20 ml). The combined extracts were dried (MgSO$_4$) and the solvent was evaporated. The residue was purified by column chromatography on silica gel (250 ml) using a mixture of heptane and ethyl acetate (2:3) as eluent, affording 0.53 g (30%) of (R)-1-(3-(10,11-dihydro-5H-dibenzo[b,f]azepin-5-yl)-1-propionyl)-3-piperidinecarboxylic acid ethyl ester.

TLC: $R_f$=0.42 (SiO$_2$:heptane/ethyl acetate=1:3).

The above ester (0.52 g, 1.28 mmol) was dissolved in ethanol (8 ml) and a solution of sodium hydroxide (0.22 g, 5.5 mmol) in water (3 ml) was added. The mixture was stirred for 30 minutes. 1 N Hydrochloric acid (5 ml) was added and the mixture was extracted with dichloromethane (2×20 ml). The combined organic extracts were washed with brine (40 ml), dried (MgSO$_4$) and the solvent was evaporated. The residue was re-evaporated twice with acetone and the residue was dissolved in warm acetone (10 ml) and left at 5° C. overnight. The precipitate was filtered off, washed with acetone and dried to give 0.31 g (63%) of the title compound.

HPLC retention time=25.12 minutes (5 μm C18 4×250 mm column, eluting with a 20–80% gradient of 0.1% trifluoroacetic acid/acetonitrile and 0.1% trifluoroacetic acid/water over 30 minutes at 35° C.).

Example 22

1-(3-(10,11-Dihydro-5H-dibenzo[b,f]azepin-5-yl)-1-propionyl)-4-piperidinecarboxylic Acid

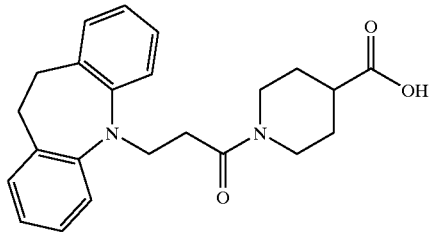

3-(10,11-Dihydro-5H-dibenzo[b,f]azepin-5-yl)-1-propionic acid ethyl ester (1.2 g, 4.0 mmol, prepared similarly as described in Example 21) was dissolved in ethanol (25 ml) and a solution of sodium hydroxide (0.78 g, 19.5 mmol) in water (5 ml) was added. The mixture was stirred for 5 h. 1 N Hydrochloric acid (20 ml) was added and the mixture was extracted with dichloromethane (2×30 ml). The combined organic extracts were washed with brine (50 ml), dried (MgSO$_4$) and the solvent was evaporated to give 1.06 g (97%) of 3-(10,11-dihydro-5H-dibenzo[b,f]azepin-5-yl)-1-propionic acid.

The above acid (1.06 g, 4.0 mmol) was dissolved in dichloromethane (25 ml), and thionyl chloride (0.94 g, 7.9 mmol) was added. The mixture was heated at reflux temperature for 2 h and evaporated to give the corresponding acid chloride. This was suspended in toluene (15 ml) and added to a solution of 4-piperidinecarboxylic acid acid ethyl ester (1.25 g, 8.0 mmol) in toluene (4 ml). The reaction mixture was heated at reflux temperature overnight. Water (10 ml) was added and the mixture was extracted with toluene (7 ml). The organic extract was dried (MgSO$_4$) and the solvent was evaporated. The residue was purified by column chromatography on silica gel (200 ml) using a mixture of heptane and ethyl acetate (2:3) as eluent, affording 0.75 g (47%) of 1-(3-(10,11-dihydro-5H-dibenzo[b,f]azepin-5-yl)-1-propionyl)-4-piperidinecarboxylic acid ethyl ester.

TLC: $R_f$=0.49 (SiO$_2$:heptane/ethyl acetate=1:3).

The above ester (0.8 g, 2.0 mmol) was dissolved in ethanol (12 ml) and a solution of sodium hydroxide (0.2 g, 5.0 mmol) in water (3 ml) was added. The mixture was stirred for 45 minutes, 1 N hydrochloric acid (7 ml) was added and the mixture was extracted with dichloromethane (2×20 ml). The combined organic extracts were washed with brine (40 ml), dried (MgSO$_4$) and evaporated. The residue was re-evaporated three times with acetone and the foamy residue was suspended in heptane (15 ml) and stirred for 1 h. The precipitate was filtered off, washed with heptane and dried. The solid was re-dissolved in warm toluene (8 ml) and left at 5° C. Petroleum ether (40–60° C., 5 ml) was added to promote precipitation, and the mixture was left at 5° C. The solid was filtered off and dried to give 0.18 g (24%) of the title compound.

HPLC retention time=25.06 minutes (5 μm C18 4×250 mm column, eluting with a 20–80% gradient of 0.1% trifluoroacetic acid/acetonitrile and 0.1% trifluoroacetic acid/water over 30 minutes at 35° C.).

Example 23

(R)-1-(2-(10,11-Dihydro-5H-dibenzo[b,f]azepin-5-ylcarbonyl)-1-benzyl)-3-piperidinecarboxylic Acid Hydrochloride

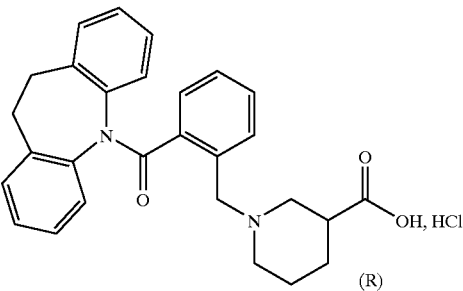

Phthalide (13.4 g, 0.1 mol) and dichlorotriphenylphosphorane (35.6 g, 0.11 mol) were mixed and heated at 180° C. for 4 h. After cooling, this mixture was added to a solution of 10,11-dihydro-5H-dibenzo[b,f]azepine in toluene (200 ml). The resulting mixture was heated at reflux temperature for 16 h. After cooling, the mixture was concentrated in vacuo. Ethyl acetate (100 ml) followed by heptane (200 ml) was added to the residue, and triphenylphosphine oxide was filtered off. The mother liquor was concentrated in vacuo and redissolved in ethyl acetate (50 ml). The solid was filtered off and dried to give 13.1 g (38%) of (2-chloromethylphenyl)-(10,11-dihydro-5H-benz[b,f]azepin-5-yl)methanone.

A mixture of the above methanone (3.0 g, 8.6 mmol), (R)-3-piperidinecarboxylic acid ethyl ester (L)-tartrate (5.3 g, 17.2 mmol), potassium carbonate (7.15 g, 52 mmol), potassium iodide (2.9 g, 17 mmol) and 2-butanone (100 ml) was heated at reflux temperature for 3 h. After cooling, the mixture was filtered and the filter cake was extracted with ethyl acetate. The combined filtrates were concentrated in vacuo. The residue was purified by column chromatography on silica gel (800 ml) using a mixture of ethyl acetate and heptane (1:2) as eluent. This afforded 3.42 g (85%) (R)-1-(2-(10,11-dihydro-dibenzo[b,f]azepine-5-carbonyl)-benzyl)-3-piperidinecarboxylic acid ethyl ester as a foam.

The above ester (3.40 g, 7.3 mmol) was dissolved in 1,4-dioxane (30 ml) and 1 N potassium hydroxide (15 ml) was added. The mixture was stirred for 3 days at room temperature. Water (50 ml) was added and the mixture was washed with diethyl ether (2×50 ml). The aqueous phase was made acidic using 1 N hydrochloric acid and was extracted with dichloromethane (2×50 ml). The combined organic extracts were dried (MgSO$_4$) and concentrated in vacuo to give 3.79 g of the title compound.

M.p.>250° C. Calculated for C$_{28}$H$_{28}$N$_2$O$_3$, HCl: C, 70.50%; H, 6.13%; N, 5.87%. Found: C, 70.42%; H, 6.28%; N, 5.43%.

Example 24

(R)-1-(2-(10,11-Dihydro-5H-dibenzo[b,f]azepin-5-ylmethyl)-benzyl)-3-piperidinecarboxylic Acid Hydrochloride

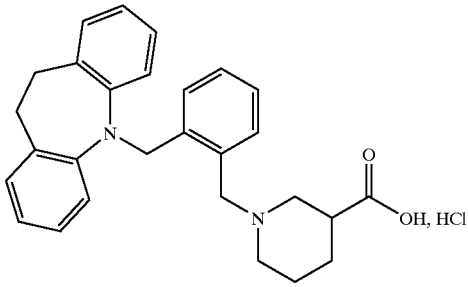

(2-Chloromethylphenyl)-(10,11-dihydro-5H-benz[b,f]azepin-5-yl)methanone (7.0 g, 20 mmol, prepared as described in Example 23) was added in portions at 5° C. to a solution of alane in tetrahydrofuran (prepared from dropwise addition of 98% sulfuric acid (1.11 ml, 20 mmol) to lithium aluminum hydride (1.53 g, 40 mmol) in tetrahydrofuran (50 ml) at 5–10° C.). When addition was complete, the mixture was stirred at 5° C. for 1 h. Water (1.33 ml) was added and the mixture was filtered. The precipitate was washed with tetrahydrofuran. The combined tetrahydrofuran washings were concentrated in vacuo to give 5.34 g of a mixture of 5-(2-methylbenzyl)-10,11-dihydro-5H-dibenzo[b,f]azepine and 5-(2-chloromethylbenzyl)-10,11-dihydro-5H-dibenzo[b,f]azepine.

A mixture of the above mixture containing 5-(2-chloromethylbenzyl)-10,11-dihydro-5H-dibenzo[b,f]azepine (3.22 g mixture containing 1.87 g, 5.8 mmol), (R)-3-piperidinecarboxylic acid ethyl ester (L)-tartrate (3.56 g, 11.6 mmol), potassium carbonate (4.8 g, 35 mmol), potassium iodide (1.9 g, 12 mmol) and 2-butanone (50 ml) was heated at reflux temperature for 2 h. After cooling, the mixture was filtered and the filter cake was extracted with ethyl acetate. The combined filtrates were concentrated in vacuo. The residue was purified by column chromatography on silica gel (800 ml) using a mixture of ethyl acetate and heptane (1:10) as eluent. This afforded 2.51 g (96%) ((R)-1-(2-(10,11-dihydro-dibenzo[b,f]azepin-5-ylmethyl)-benzyl)-3-piperidinecarboxylic acid ethyl ester as an oil.

The above ester (2.5 g, 5.5 mmol) was dissolved in 1,4-dioxane (50 ml) and 1 N potassium hydroxide (10 ml) was added. The mixture was stirred at reflux temperature for 16 h. Water (100 ml) was added and the mixture was washed with diethyl ether (50 ml). The aqueous phase was made acidic using 5 N hydrochloric acid and was extracted with dichloromethane (2×100 ml). The combined organic extracts were dried (MgSO$_4$) and concentrated in vacuo. The residue was triturated with diethyl ether (20 ml) and dried. This afforded 1.72 g (68%) of the title compound.

M.p.: amorph. Calculated for C$_{28}$H$_{30}$N$_2$O$_2$, HCl, 0.5 H$_2$O: C, 71.25%; H, 6.83%; N, 5.93%. Found: C, 71.09%; H, 7.08%; N, 5.47%.

Example 25

(R)-1-(3-(10,11-Dihydro-5H-dibenzo[a,d]cyclohepten-5-yl)-3-oxo-1-propyl)-3-piperidinecarboxylic Acid

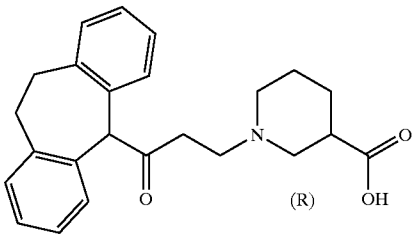

(R)-1-(3-(10,11-Dihydro-5H-dibenzo[a,d]cyclohepten-5-ylidene)-1-propyl)-3-piperidine-carboxylic acid (5.5 g, 15.2 mmol, prepared as described in WO9518793) was dissolved in formic acid (20 ml) and 35% hydrogen peroxide (5 ml) was added. The resulting mixture was stirred at room temperature for 16 h and concentrated in vacuo. The residue was partitioned between water (50 ml) and ethyl acetate (100 ml). The aqueous phase was concentrated in vacuo to give 2.8 g of (R)-1-(3-hydroxy-3-(5-hydroxy-10,11-dihydro-5H-dibenzo[a,d]-cyclohepten-5-yl)-1-propyl)-3-piperidinecarboxylic acid as a foam.

The above 3-piperidinecarboxylic acid (2.84 g, 5.3 mmol) was dissolved in dichloromethane (200 ml), methanesulfonic acid (0.5 ml) was added and the resulting mixture was heated at reflux temperature for 2 days. The mixture was allowed to cool and was then concentrated in vacuo. The residue was dissolved in water (50 ml) and extracted with dichloromethane (4×50 ml). The combined organic extracts were concentrated in vacuo. The residue was purified by column chromatography on silica gel using a mixture of dichloromethane and methanol (9:1) as eluent. This afforded after evaporation of the solvent 0.74 g of the title compound.

LCMS (m/z) 378 (MH$^+$).

Example 26

1-(3-(3-Chloro-10,11-dihydro-5H-dibenzo[b,f]azepin-5-yl)-(2R)-methylpropyl)-4-piperidinecarboxylic Acid Hydrochloride

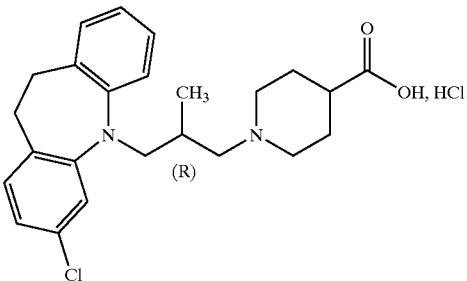

3-Chloro-10,11-dihydro-5H-dibenzo[b,f]azepine (2.0 g, 8.7 mmol) was dissolved in N,N-dimethylformamide. Sodium hydride (0.52 g, 13 mmol, 60% dispersion in oil) was added in portions and the mixture was heated at 50° C. for 3 h. 3-Bromo-(2R)-methyl-1-(2-tetrahydropyranyloxy) propane (4.13 g, 17.4 mmol) was added and the reaction mixture was stirred at room temperature overnight. Stirring was continued at 50° C. for 4.5 h. Additional bromide (2.9 g, 12 mmol) was added and stirring was continued at 60° C. overnight and at room temperature for 48 h. The mixture was poured into water (300 ml) and extracted with diethyl ether (3×150 ml). The solvent was evaporated and the residue was dissolved in methanol (50 ml). 6 N Hydrochloric acid (30 ml) was added and the mixture was heated at reflux temperature for 30 minutes. After cooling, the mixture was poured into water (500 ml) and extracted with ethyl acetate (3×150 ml). The combined organic phases were washed with saturated sodium bicarbonate, dried (MgSO$_4$) and evaporated. The residue was purified by column chromatography on silica (100 g) using dichloromethane as eluent. This afforded crude 3-chloro-5-(3-hydroxy-(2S)-methylpropyl)-10,11-dihydro-5H-dibenzo[b,f]azepine (0.5 g) which was dissolved in N,N-dimethylformamide (2 ml). Piperidine (0.32 g) was added and the mixture was stirred for 3 h. Toluene (100 ml) was added followed by 1 N hydrochloric acid (10 ml) and the phases were separated. The aqueous phase was extracted with toluene (80 ml) and the combined organic phases were washed with brine (5 ml) and dried (MgSO$_4$). The solvent was evaporated to give 0.4 g (15%) of crude 3-chloro-5-(3-hydroxy-(2S)-methylpropyl)-10,11-dihydro-5H-dibenzo[b,d]azepine.

TLC: R$_f$=0.23 (SiO$_2$:dichloromethane).

The above alcohol (1.25 g, 4.14 mmol) was dissolved in toluene (40 ml) and triethylamine (1.05 g, 10.4 mmol) was added. The mixture was cooled on an ice-water bath, and a solution of methanesulfonyl chloride (0.95 g, 8.3 mmol) in toluene (10 ml) was added dropwise. After stirring at 0° C. for 1 h, stirring was continued at room temperature for 1 h. Water (15 ml) and toluene (25 ml) was added and the phases were separated. The aqueous phase was extracted with toluene (25 ml). The combined organic phases were washed with brine (10 ml), dried (MgSO$_4$) and the solvent was evaporated. The residue was dissolved in methyl ethyl ketone (10 ml) and potassium carbonate (0.86 g, 6.21 mmol) and 4-piperidinecarboxylic acid ethyl ester (0.85 g, 5.38 mmol) were added. The reaction mixture was heated at reflux temperature overnight. After cooling, the mixture was filtered and the solvent was evaporated. The residue was first purified by column chromatography on silica (50 g) using dichloromethane as eluent, and then further purified by column chromatography on silica gel (5 g) using a mixture of ethyl acetate and dichloromethane (2:8) as eluent. Heptane was added and the precipitated solid was filtered off, affording 0.072 g (4%) of 1-(3-(3-chloro-10,11-dihydro-5H-dibenzo[b,f]azepin-5-yl)-(2R)-methylpropyl)-4-piperidinecarboxylic acid ethyl ester.

TLC: R$_f$=0.28 (SiO$_2$:dichloromethane/ethyl acetate=8:2).

The above ethyl ester (0.072 g, 0.163 mol) was dissolved in ethanol (3 ml). 4 N Sodium hydroxide (0.18 ml, 0.72 mmol) was added, and the reaction mixture was stirred for 4 h at room temperature. 4 N Hydrochloric acid (0.225 ml) was added followed by water (3 ml) and the mixture was extracted with dichloromethane (100 ml). The organic phase was dried (MgSO$_4$) and the solvent was evaporated. The residue was stripped with dichloromethane (2×5 ml) and acetone (3×5 ml). Isopropyl acetate (2 ml) was added, and the mixture was evaporated. The residue was re-dissolved in acetone (2×3 ml) twice and evaporated to give 0.16 g (22%) of the title compound.

HPLC retention time=24.14 minutes (5 μm C18 4×250 mm column, eluting with a 20–80% gradient of 0.1% trifluoroacetic acid/acetonitrile and 0.1% trifluoroacetic acid/water over 30 minutes at 35° C.).

Example 27

1-(3-(10,11-Dihydro-5H-dibenzo[b,f]azepin-5-yl)-2-hydroxy-propyl)-4-piperidinecarboxylic Acid Hydrochloride

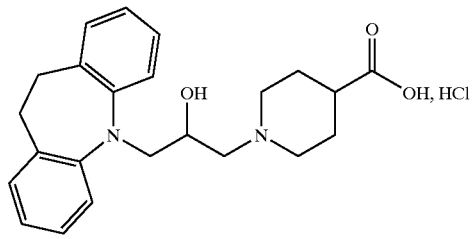

A mixture of crude (10,11-dihydro-5H-dibenzo[b,f] azepin-5-yl)-2,3-epoxypropane (22.6 g, 90 mmol, prepared as described in Example 19) and 4-piperidinecarboxylic acid ethyl ester (14.15 g, 90 mmol) in dry 2-butanone (50 ml) was stirred and heated at reflux temperature for 24 h. The solvent was removed in vacuo and the residue was dissolved in toluene (250 ml) and water (250 ml). The pH was adjusted to 6 by addition of 1 N hydrochloric acid. The organic phase was separated, washed with water (3×100 ml), dried (MgSO$_4$) and concentrated in vacuo. The crude product was purified by column chromatography on silica gel using a mixture of toluene, ethyl acetate and triethylamine (20:20:1) as eluent to give 5.8 g (16%) of 1-(3-(10,11-dihydro-5H-dibenzo[b,f]azepin-5-yl)-2-hydroxy-propyl)-4-piperidinecarboxylic acid ethyl ester as an oil.

TLC: R$_f$=0.28 (SiO$_2$:toluene/ethyl acetate/triethylamine=20:20:1)

The above ester (0.46 g, 1.13 mmol) was dissolved in ethanol (5 ml), 2 N sodium hydroxide (1.87 ml, 3.73 mmol) was added and the homogeneous mixture was stirred at room temperature for 24 h. Water (15 ml) was added and the ethanol was removed in vacuo. The aqueous solution was washed with ether (2×10 ml) and pH was adjusted to 6 by addition of 1N hydrochloric acid. The acidic mixture was extracted with dichloromethane (2×15 ml). The combined organic extracts were washed with water (20 ml), dried (MgSO$_4$) and concentrated in vacuo. The residue was triturated with ether and the product collected by filtration to give 0.26 g (55%) of the title compound as an amorphous powder.

HPLC retention time=15.36 minutes (5 μm C18 4×250 mm column, eluting with a 20–80% gradient of 0.1% trifluoroacetic acid/acetonitrile and 0.1% trifluoroacetic acid/water over 30 minutes at 35° C.). Calculated for $C_{23}H_{28}N_2O_3$, HCl, 0.75 $H_2O$: C, 64.18%; H, 7.14%; N, 6.51% Found: C, 64.22%; H, 7.28%; N, 6.10%.

Example 28

(R)-1-(3-(10,11-Dihydro-5H-dibenzo[b,f]azepin-5-yl)-2-hydroxypropyl)-3-piperidinecarboxylic Acid

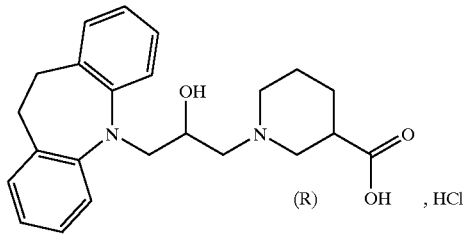

A mixture of crude (10,11-dihydro-5H-dibenzo[b,f]azepin-5-yl)-2,3-epoxypropane (6.0 g, 20.8 mmol, prepared as described in Example 19), (R)-3-piperidinecarboxylic acid ethyl ester (L)-tartrate (6.24 g, 20.8 mmol), potassium carbonate (11.5 g, 83.2 mmol) and sodium iodide (3.12 g, 20.8 mmol) in dry N,N-dimethylformamide (25 ml) was stirred and heated at 60° C. for 48 h. The reaction mixture was concentrated in vacuo and the residue dissolved in toluene (100 ml) and ethyl acetate (100 ml). The solution was washed with water (2×50 ml), dried (MgSO$_4$) and concentrated in vacuo. The crude product was purified by column chromatography on silica gel using a mixture of toluene, ethyl acetate and triethylamine (35:6:1) as eluent to give 4.5 g (53%) of (R)-1-(3-(10,11-dihydro-5H-dibenzo[b,f]azepin-5-yl)-2-hydroxy-propyl)-3-piperidinecarboxylic acid ethyl ester as an oil.

TLC: R$_f$=0.41 (SiO$_2$:toluene/ethyl acetate/triethylamine=20:20:1)

The above ester (0.38 g, 0.93 mmol) was dissolved in ethanol (5 ml), 2 N sodium hydroxide (1.54 ml, 3.07 mmol) was added and the homogeneous mixture was stirred at room temperature for 24 h. Water (15 ml) was added and the ethanol was removed in vacuo. The aqueous solution was washed with ether (2×10 ml) and pH was adjusted to 6 by addition of 1N hydrochloric acid. The acidic mixture was extracted with dichloromethane (2×15 ml). The combined organic extracts were washed with water (20 ml), dried (MgSO$_4$) and concentrated in vacuo. The residue was triturated with ether and the product collected by filtration to give 0.23 g (66%) of the title compound as a powder.

HPLC retention time=18.28 minutes (5 μm C18 4×250 mm column, eluting with a 20–80% gradient of 0.1% trifluoroacetic acid/acetonitrile and 0.1% trifluoroacetic acid/water over 25 minutes at 35° C.). Calculated for $C_{23}H_{28}N_2O_3$, 0.5 $H_2O$: C, 70.93%; H, 7.50%; N, 7.19% Found: C, 71.17%; H, 7.45%; N, 7.12%.

Example 29

1-(3-(10,11-Dihydro-5H-dibenzo[b,f]azepin-5-yl)-2-propoxypropyl)-4-piperidinecarboxylic Acid Hydrochloride

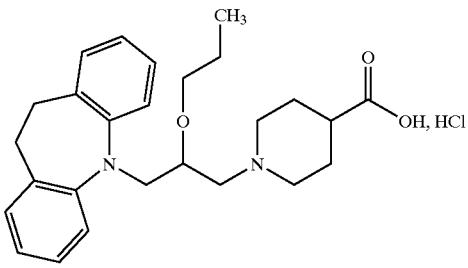

Sodium hydride (60% oil suspension, 0.108 g, 2.7 mmol) was added to a stirred solution of 1-(3-(10,11-dihydro-5H-dibenzo[b,f]azepin-5-yl)-2-hydroxy-propyl)-4-piperidinecarboxylic acid ethyl ester (1.1 g, 2.7 mmol) in dry N,N-dimethylformamide (7.5 ml). Propylbromide (0.7 g, 5.68 mmol) was added dropwise to the ice-cooled stirred solution and the reaction mixture was left at room temperature for 16 h. The mixture was concentrated in vacuo. The residue was dissolved in toluene (20 ml), washed with water (3×10 ml), dried (MgSO$_4$) and concentrated in vacuo. The crude product was purified by column chromatography on silica gel using a mixture of toluene, ethyl acetate and triethylamine (35:6:1) as eluent to give 0.11 g (9%) of 1-(3-(10,11-dihydro-5H-dibenzo[b,f]azepin-5-yl)-2-propoxypropyl)-4-piperidinecarboxylic acid ethyl ester as an oil.

The above ester (0.11 g, 0.244 mmol) was dissolved in ethanol (2 ml), 2 N sodium hydroxide (0.41 ml, 0.82 mmol) was added and the homogeneous mixture was stirred at room temperature for 16 h. Water (10 ml) was added and the ethanol was removed in vacuo. The aqueous solution was adjusted to pH 6 by addition of 1 N hydrochloric acid, and extracted with dichloromethane (2×10 ml). The combined organic phases were washed with water (20 ml), dried (MgSO$_4$) and concentrated in vacuo. The residue was dissolved in tetrahydrofuran (2.5 ml), 2.6 N hydrochloric acid (0.11 ml) was added and the solution was poured into ether (25 ml). After standing overnight the precipitated product was collected by filtration to give 0.095 g (85%) of the title compound as a powder.

M.p. 198–203° C.; Calculated for $C_{26}H_{342}O_3$, HCl, 0.25 $H_2O$: C, 67.37%; H, 7.72%; N, 6.04% Found: C, 67.20%; H, 7.93%; N, 5.60%.

Example 30

(R)-1-(2-(N-(10,11-dihydro-5H-dibenzo[a,d]cyclohepten-5-yl)-N-methylamino)ethyl)-3-piperidinecarboxylic Acid

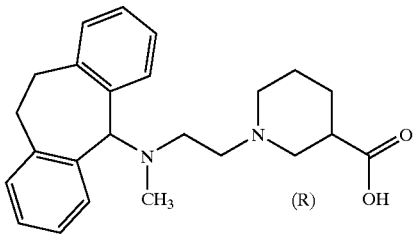

A mixture of (R)-1-(2-bromoethyl)-3-piperidinecarboxylic acid ethyl ester hydrobromide (5.0 g, 14.5 mmol), N-(10,11-dihydro-5H-dibenzo[a,d]cyclohepten-5-yl)-N-methylamine hydrochloride (3.8 g, 14.6 mmol, prepared as described in Neth.Appl. 6 500 085), potassium carbonate (7.0 g, 50 mmol) and methyl ethyl ketone (150 ml) was heated and stirred at 80° C. for 24 h. The mixture was filtered and the solvent was removed by evaporation in vacuo. The crude residue was purified by column chromatography on silica gel (50 g) first using chloroform and then ethyl acetate as eluents. This afforded 3.15 g (53%) of (R)-1-(2-(N-methyl-N-(10,11-dihydro-5H-dibenzo[a,d]cyclohepten-5-yl)amino)ethyl)-3-piperidinecarboxylic acid ethyl ester as an oil.

TLC: $R_f$=0.40 ($SiO_2$:chloroform/ethanol/ammoniumhydroxide=20:1:0.1).

The above ester (2.95 g, 7.3 mmol) was dissolved in ethanol (40 ml) and 5 N sodium hydroxide (2.5 ml) was added. The mixture was stirred at 40° C. for 24 h and ethanol was evaporated in vacuo. Water (40 ml) followed by acetic acid (2.5 ml) were added and the solution was extracted with dichloromethane (2×50 ml). The combined organic extratcts were dried ($MgSO_4$) and the solvent was evaporated in vacuo. The residue was triturated with diethyl ether to give 2.4 g (87%) of the title compound.

M.p. 187–190° C. Calculated for $C_{24}H_{30}N_2O_2$, 0.25 $H_2O$: C, 75.26%; H, 8.03%; N, 7.31% Found: C, 74.94%; H, 7.98%; N, 7.16%.

What is claimed is:

1. A compound of formula I

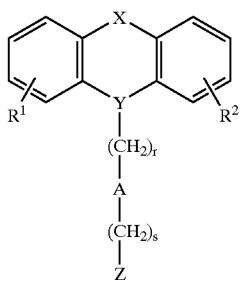

(I)

wherein $R^1$ and $R^2$ are hydrogen; and

X is —$CH_2CH_2$— or —CH=CH—; and

Y is N; and r and s independently are 0, 1, 2, 3 or 4; and

A is —($CR^9R^{10}$)— wherein $R^9$ and $R^{10}$ independently are hydrogen, $C_{1-6}$-unbranched alkyl, $C_{3-6}$-branched alkyl or $C_{3-7}$-cycloalkyl, such that when A is —$CH_2$—, r+s≦3; and Z is selected from

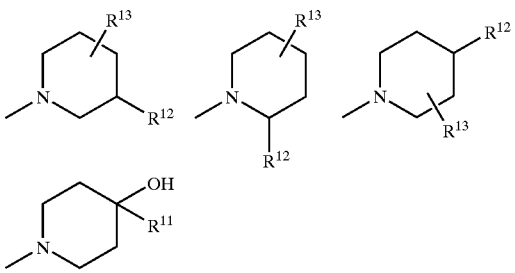

and $R^{11}$ is $C_{3-6}$-alkyl or $C_{1-6}$-alkoxy; and $R^{12}$ is —($CH_2$)$_p$$COR^{17}$ wherein p is 0 or 1; and wherein $R^{17}$ is —OH, —$NHR^{20}$ or $C_{1-6}$-alkoxy, wherein $R^{20}$ is hydrogen or $C_{1-6}$-alkyl; and $R^{13}$ is hydrogen, halogen, trifluoromethyl, hydroxy, $C_{1-6}$-alkyl or $C_{1-6}$-alkoxy;

or a pharmaceutically acceptable salt thereof;

provided that when A is —$CH_2$— and r+s is ≦3, Z cannot be

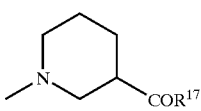

wherein $R^{17}$ is —OH or $C_{1-6}$-alkoxy.

2. A compound according to claim 1 wherein r is 0, 1 or 2.

3. A compound according to claim 1 wherein s is 0, 1 or 2.

4. A compound according to claim 1 wherein Z is selected from

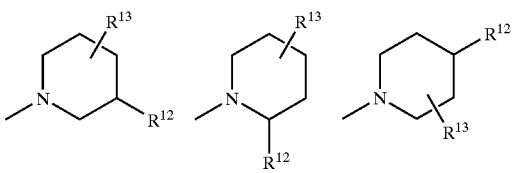

5. A compound according to claim 1 wherein $R^{12}$ is —($CH_2$)$_p$$COR^{17}$ wherein p is 0 or 1 and $R^{17}$ is —OH.

6. A compound according to claim 1 selected from the following:

1-(3-(10,11-Dihydro-5H-dibenzo[b,f]azepin-5-yl)-(2R)-methyl-1-propyl)-(3R)-piperidinecarboxylic acid;

1-(3-(10,11-Dihydro-5H-dibenzo[b,f]azepin-5-yl)-(2R)-methyl-1-propyl)-4-piperidinecarboxylic acid;

1-(3-(10,11-Dihydro-5H-dibenzo[b,f]azepin-5-yl)-(2R)-methyl-1-propyl)-(2R)-piperidinecarboxylic acid;

(R)-1-(3-(10,11-Dihydro-5H-dibenzo[b,f]azepin-5-yl)1-methylpropyl)-3-piperidinecarboxylic acid;

(R)-1-(2-(10,11-dihydro-5H-dibenzo[b,f]azepin-5-yl)-1-methyl-ethyl)-3-piperidinecarboxylic acid;

(R)-1-(2-(10,11-Dihydro-5H-dibenzo[b,f]azepin-5-ylmethyl)-1-pentyl)-3-piperidinecarboxylic acid;

or a pharmaceutically acceptable salt thereof.

7. A pharmaceutical composition comprising a compound according to claim 1 together with a pharmaceutically acceptable carrier or diluent.

8. A method of treating neurogenic inflammation in a subject in need of such treatment comprising administering to said subject an effective amount of a compound according to claim 1.

* * * * *